US009238604B2

(12) United States Patent
Xu et al.

(10) Patent No.: US 9,238,604 B2
(45) Date of Patent: Jan. 19, 2016

(54) PROCESS AND INTERMEDIATES FOR PREPARING MACROLACTAMS

(75) Inventors: Feng Xu, Staten Island, NY (US); Guy Humphrey, Hillsborough, NJ (US); Tao Pei, Morganville, NJ (US); Zhiguo Jake Song, Edison, NJ (US); Tao Wang, Berkeley Heights, NJ (US); Laura Artino, Oakhurst, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/239,393

(22) PCT Filed: Aug. 16, 2012

(86) PCT No.: PCT/US2012/051177
§ 371 (c)(1),
(2), (4) Date: Feb. 18, 2014

(87) PCT Pub. No.: WO2013/028470
PCT Pub. Date: Feb. 28, 2013

(65) Prior Publication Data
US 2014/0200343 A1 Jul. 17, 2014

Related U.S. Application Data

(60) Provisional application No. 61/539,540, filed on Sep. 27, 2011, provisional application No. 61/533,915, filed on Sep. 13, 2011, provisional application No. 61/533,439, filed on Sep. 12, 2011, provisional application No. 61/525,462, filed on Aug. 19, 2011.

(51) Int. Cl.

| | |
|---|---|
| *C07K 5/08* | (2006.01) |
| *C07K 5/10* | (2006.01) |
| *C07K 5/12* | (2006.01) |
| *C07D 401/12* | (2006.01) |
| *C07C 35/04* | (2006.01) |
| *C07K 5/083* | (2006.01) |
| *C07D 403/12* | (2006.01) |
| *C07D 498/16* | (2006.01) |
| *C07C 67/14* | (2006.01) |
| *C07C 69/013* | (2006.01) |
| *C07C 69/12* | (2006.01) |
| *C07C 269/04* | (2006.01) |
| *C07C 271/34* | (2006.01) |
| *A61K 38/00* | (2006.01) |

(52) U.S. Cl.
CPC .................. *C07C 35/04* (2013.01); *C07C 67/14* (2013.01); *C07C 69/013* (2013.01); *C07C 69/12* (2013.01); *C07C 269/04* (2013.01); *C07C 271/34* (2013.01); *C07D 403/12* (2013.01); *C07D 498/16* (2013.01); *C07K 5/0808* (2013.01); *C07K 5/126* (2013.01); *A61K 38/00* (2013.01)

(58) Field of Classification Search
CPC .............. C07K 5/08; C07K 5/10; C07K 5/12; C07D 401/12
USPC ........................................... 540/456; 544/354
See application file for complete search history.

(56) References Cited

U.S. PATENT DOCUMENTS

| | | | |
|---|---|---|---|
| 4,871,868 | A | 10/1989 | Saito et al. |
| 5,715,960 | A | 2/1998 | Seymour |
| 7,507,262 | B2 | 3/2009 | Lim et al. |
| 2003/0186939 | A1 | 10/2003 | Tani et al. |
| 2009/0155209 | A1 | 6/2009 | Blatt et al. |
| 2009/0216016 | A1 | 8/2009 | Yoshida et al. |
| 2009/0286778 | A1 | 11/2009 | Combs et al. |
| 2010/0029666 | A1 | 2/2010 | Harper et al. |

FOREIGN PATENT DOCUMENTS

| | | |
|---|---|---|
| WO | WO2006102087 | 9/2006 |
| WO | WO2006119061 | 11/2006 |
| WO | WO2007015787 | 2/2007 |
| WO | WO2007015855 | 2/2007 |
| WO | WO2007016441 | 2/2007 |
| WO | WO2007131966 | 11/2007 |
| WO | WO2007148135 | 12/2007 |
| WO | WO2008051477 | 5/2008 |
| WO | WO2008051514 | 5/2008 |
| WO | WO2008057208 | 5/2008 |
| WO | WO2008057209 A1 | 5/2008 |
| WO | WO2009010804 | 1/2009 |
| WO | WO2009108507 | 9/2009 |
| WO | WO2009134624 | 11/2009 |

(Continued)

OTHER PUBLICATIONS

Bassan et al, Multikilogram-Scale Synthesis of a Chiral Cyclopropanol and an Investigation of the Safe Use of Lithium Acetylide-Ethylene Diamine Complex, Org. Process Res. Dev., 2012, 87-95, 16.

(Continued)

*Primary Examiner* — Bruck Kifle

(74) *Attorney, Agent, or Firm* — Jule M. Lake; Laura M. Ginkel

(57) ABSTRACT

The present invention includes compounds useful as intermediates in the preparation of macrolactams, methods for preparing the intermediates, and methods for preparing macrolactams from the intermediates. One use of the methods and intermediates described herein is in the production of macrolactam compounds able to inhibit HCV NS3 protease activity. HCV NS3 inhibitory compounds have therapeutic and research applications.

8 Claims, 3 Drawing Sheets

(56) References Cited

FOREIGN PATENT DOCUMENTS

| WO | WO2010011566 | 1/2010 |
| WO | WO2011014487 | 2/2011 |
| WO | WO2013028465 | 2/2013 |
| WO | WO2013028470 | 2/2013 |
| WO | WO2013028471 | 2/2013 |

OTHER PUBLICATIONS

C. Balsano, Recent Advances in Antiviral Agents: Established and Innovative Therapies for Viral Hepatitis, Mni-Reviews in Medicinal Chemistry, 2008, pp. 307-318, 8(4).

De Francesco, Approaching a new era for hepatitis C virus therapy: inhibitors of the NS3-4A serine protease and the NS5B RNA-dependent RNA polymerase, Antiviral Research, 2003, 1-16, 58.

Gallinari et al, Modulation of Hepatitis C Virus NS3 Protease and Helicase Activities through the Interaction with NS4A, Biochemistry, 1999, 5620-5632, 38.

Gallinari et al, Multiple Enzymatic Activities Associated with Recombinant NS3 Protein of Hepatitis C Virus, J. Virol., 1998, 6758-6759, 72, No. 8.

Liverton et al, MK-7009, a Potent and Selective Inhibitor of Hepatitis C Virus NS3/4A Protease, Antimicrobial Agents and Chemotherapy, 2010, 305-311, 54, No. 1.

Liverton et al, Molecular Modeling Based Approach to Potent P2-P4 Macrocyclic Inhibitors of Hepatitis C NS3/4A Protease, J. Am. Chem. Soc., 2008, 4607-4609, 130.

Mao, A time-resolved, internally quenched fluorescence assay to characterize inhibition of hepatitis C virus nonstructural protein 3-4A protease of low enzyme concentrations, Analytical Biochemistry, 2008, 1-8, 373.

Ronn, New Developments in the Discovery of Agents to Treat Hepatitis C, Current Topics in Medicinal Chemistry, 2008, 533-562, 8.

Sarges et al, 4-Amino[1,2,4]triazolo[4,3-a]quinoxalines. A Novel Class of Potent Adenosine Receptor Antagonists and Potential Rapid-Onset Antidepressants, J. Med. Chem., 1990, 2240-2254, 33.

Sheldon, Novel protease and polymerase inhibitors for the treatment of hepatitis C virus infection, Expert Opinion Investig. Drugs, 2007, 1171-1181, 16(8).

Shirakawa et al, Preparation of (E)-1-Alkenylboronic Acid Pinacol Esters via Transfer of Alkenyl Group from Boron to Boron, Synthesis, 2004, 1814-1820, 11.

Song et al, Synthesis of Vaniprevir (MK-7009): Lactamization to Prepare a 22-Membered Macrocycle, J. Org. Chem., 2011, 7804-7815, 76.

Steven S. Carroll, Inhibition of Hepatitis C Virus RNA Replication by 2'-Modified Nucleoside Analogs, NPL-CARROLL-11979, 2003, pp. 11979-11984, 278(14).

Taliani et al, A Continuous Assay of Hepatitis C Virus Protease Based on Resonance Energy Transfer Depsipeptide Substrates, Anal. Biochem., 1996, 60-67, 240.

PROCESS AND INTERMEDIATES FOR PREPARING MACROLACTAMS

CROSS-REFERENCE TO RELATED APPLICATIONS

This application is a National Stage application of International Patent Application No. PCT/US2012/051177, filed Aug. 16, 2012, which claims the benefit of U.S. Provisional Patent Application No. 61/525,462, filed Aug. 19, 2011, U.S. Provisional Patent Application No. 61/533,439, filed Sep. 12, 2011, U.S. Provisional Patent Application No. 61/533,915, filed Sep. 13, 2011, and U.S. Provisional Patent Application No. 61/539,540, filed Sep. 27, 2011.

FIELD OF THE INVENTION

The present invention relates to process and intermediates that can be used for preparing macrolactams. One use of the methods and intermediates described herein is the production of macrolactam compounds able to inhibit HCV NS3 protease activity. HCV NS3 inhibitory compounds have therapeutic and research applications.

BACKGROUND OF THE INVENTION

Hepatitis C virus (HCV) infection is a major health problem. HCV infection leads to chronic liver disease, such as cirrhosis and hepatocellular carcinoma, in a substantial number of infected individuals. Several virally-encoded enzymes are putative targets for therapeutic intervention, including a metalloprotease (NS2-3), a serine protease (NS3), a helicase (NS3), and an RNA-dependent RNA polymerase (NS5B).

Potential treatments for HCV infection are discussed in different references including Balsano, *Mini Rev. Med. Chem.* 8(4):307-318, 2008, Rönn et al., *Current Topics in Medicinal Chemistry* 8:533-562, 2008, Sheldon et al., *Expert Opin. Investig. Drugs* 16(8):1171-1181, 2007, and De Francesco et al., *Antiviral Research* 58:1-16, 2003.

Examples of publications describing macrolactam compounds able to inhibit HCV protease activity include McCauley et al., WO2011014487; Harper et al., WO2010011566; Liverton et al., WO2009134624; McCauley et al., WO2009108507; Liverton et al., WO2009010804; Liverton et al., WO2008057209; Liverton et al., WO2008051477; Liverton et al., WO2008051514; Liverton et al., WO2008057208; Crescenzi et al., WO2007148135; Di Francesco et al., WO2007131966; Holloway et al., WO2007015855; Holloway et al., WO2007015787; Holloway et al., WO2007016441; Holloway et al., WO2006119061; Liverton et al., *J. Am. Chem. Soc.*, 130: 4607-4609, 2008; and Liverton et al., *Antimicrobial Agents and Chemotherapy* 54:305-311, 2010.

SUMMARY OF THE INVENTION

The present invention includes compounds useful as intermediates in the preparation of macrolactams, methods for preparing the intermediates, and methods for preparing macrolactams. One use of the methods and intermediates described herein is the production of macrolactam compounds able to inhibit HCV NS3 protease activity. HCV NS3 inhibitory compounds have therapeutic and research applications.

An example of a HCV inhibitory compound that may be produced using the procedures and intermediates described herein is Compound A, or a pharmaceutically salt thereof:

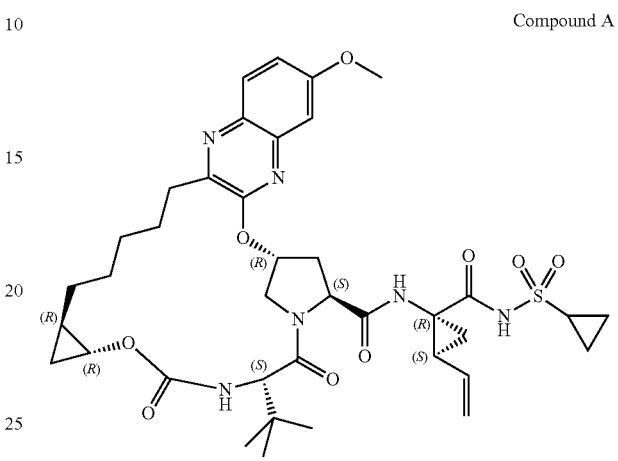

Compound A

A first aspect is directed to method of making Compound A comprising the step of coupling

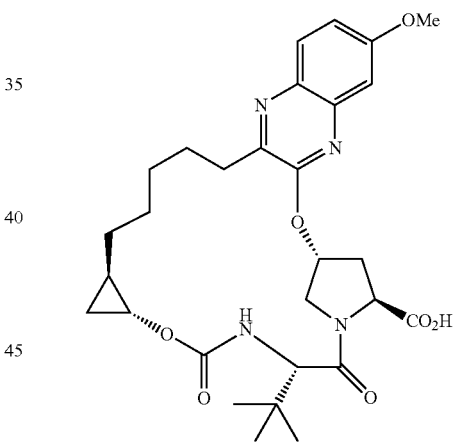

or salt thereof, to

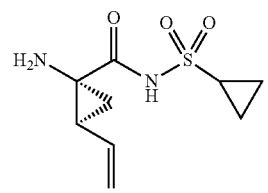

or salt thereof, to form Compound A or salt thereof, wherein the coupling comprises the use of a coupling reagent and pyridine or a pyridine derivative.

Another aspect of the invention is directed to a compound having the structure of Formula I or a salt thereof:

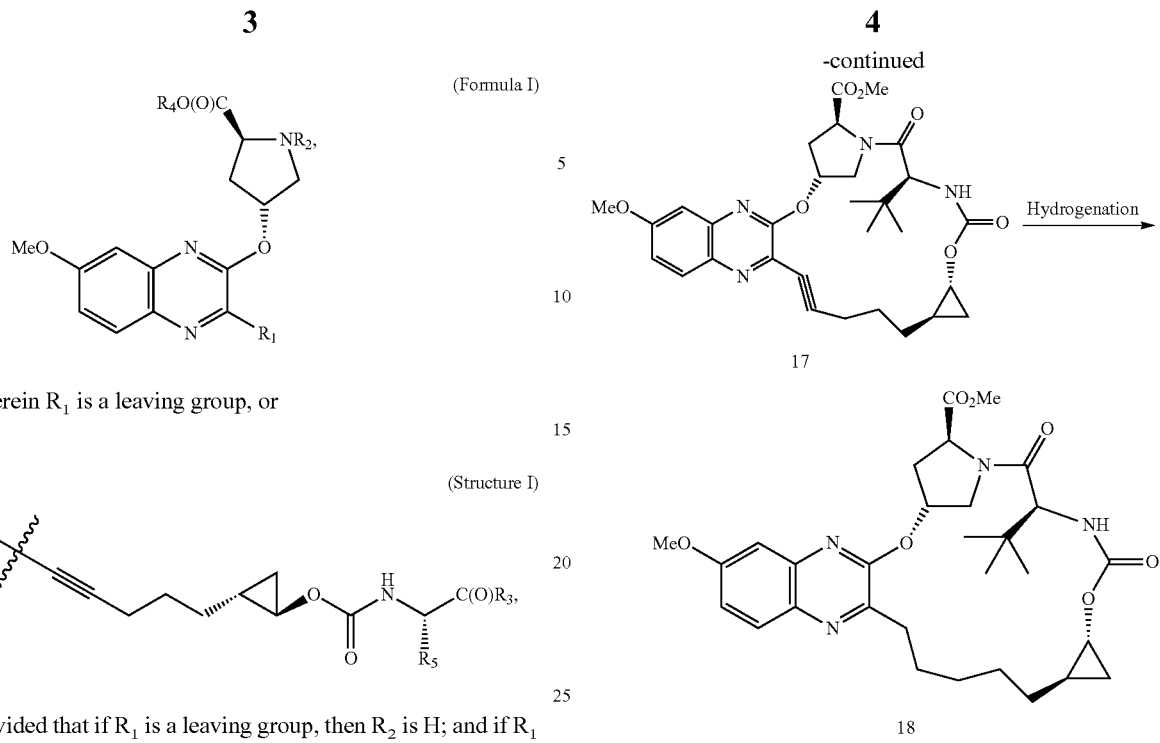

wherein $R_1$ is a leaving group, or provided that if $R_1$ is a leaving group, then $R_2$ is H; and if $R_1$ is Structure I, then $R_2$ is H and $R_3$ is OH, or $R_2$ and $R_3$ are joined together as a covalent bond;

$R_4$ is either $C_{1-6}$ alkyl or aryl; and $R_5$ is either a $C_{1-8}$ alkyl or $C_{3-8}$ cycloalkyl.

Additional aspects of the present invention are directed to a method of making a compound of Formula I.

Another aspect of the present invention is directed to a method of making Compound 18 comprising the steps of:

Another aspect of the present invention is directed to a method of making Compound 18 comprising the steps of:

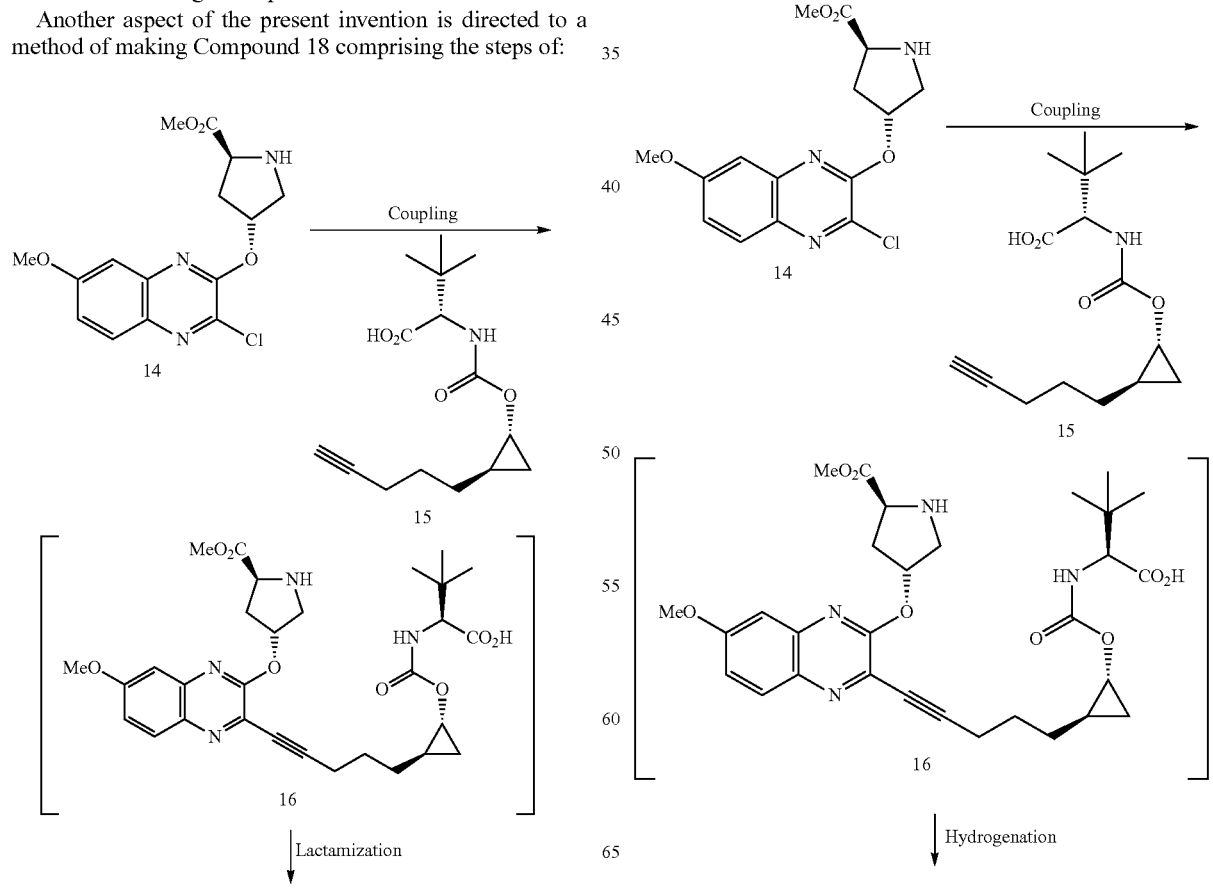

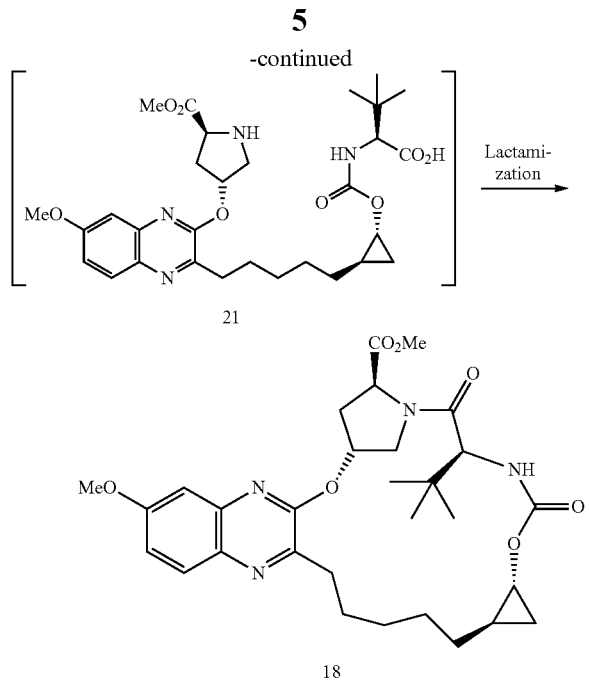

Additional aspects of the present include different forms of Compound A, Compound 14 and Compound 19.

Other embodiments, aspects and features of the present invention are either further described herein or will be apparent from the ensuing description, examples and appended claims.

DETAILED DESCRIPTION OF THE INVENTION

Figure 1:
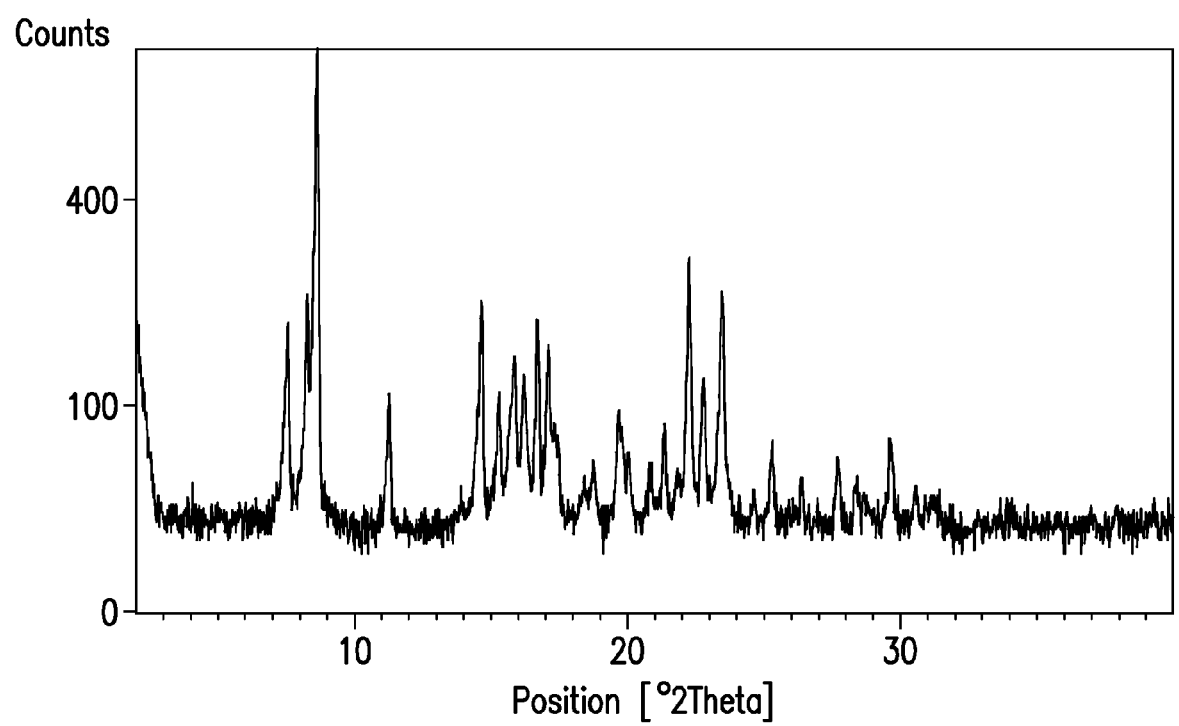
FIG. 1 illustrates an X-ray diffraction pattern of Compound 19 hydrate 1.

The methods and intermediates described herein can be used to synthesize macrolactams such as Compound A and compounds varying from Compound A by one or more functional group.

Functional groups that can be modified include a different alkyl in place of the t-butyl group, and alteration of the cyclopropylsulfonyl functional group (e.g., with an ethyl group replacing the ethylene and/or a methylcyclopropyl group replacing the cyclopropyl group).

Different intermediates and synthesis protocols are illustrated herein where Compound A was ultimately obtained. However, it is understood that based on the guidance provided herein other macrolactams can be produced using appropriate intermediates and by adding or modifying different functional groups. Examples of different macrolactams having different functional groups are provided in McCauley et al., WO2011014487; Harper et al., WO2010011566; Liverton et al., WO2009134624; McCauley et al., WO2009108507; Liverton et al., WO2009010804; Liverton et al., WO2008057209; Liverton et al., WO2008051477; Liverton et al., WO2008051514; Liverton et al., WO2008057208; Crescenzi et al., WO2007148135; Di Francesco et al., WO2007131966; Holloway et al., WO2007015855; Holloway et al., WO2007015787; Holloway et al., WO2007016441; Holloway et al., WO2006119061; Liverton et al., *J. Am. Chem. Soc.,* 130:4607-4609, 2008; and Liverton et al., *Antimicrobial Agents and Chemotherapy* 54:305-311, 2010.

Harper et al., WO2010011566 describes an alternative method for making Compound A. Harper et al., WO2010011566 et al., also includes data illustrating the ability of Compound A to inhibit HCV replicon activity and NS3/4A.

Macrolactam compounds able to inhibit HCV activity have different uses including inhibiting HCV activity in vivo, inhibiting HCV activity in vitro, and inhibiting HCV NS3 enzymatic activity. In vivo inhibition of HCV activity can be used for therapeutic applications. Inhibiting HCV activity in vitro has different applications including being used to obtain HCV resistant mutants, further characterizing the ability of a functional group to inhibit HCV replicon or enzymatic activity, and studying HCV replication or protease activity.

Macrocyclic Acid

Scheme A illustrates an overall scheme that can used to produce a macrolactam. Different aspects and embodiments of Scheme A are directed to each of the different steps, alone or in any combination with up stream or downstream steps.

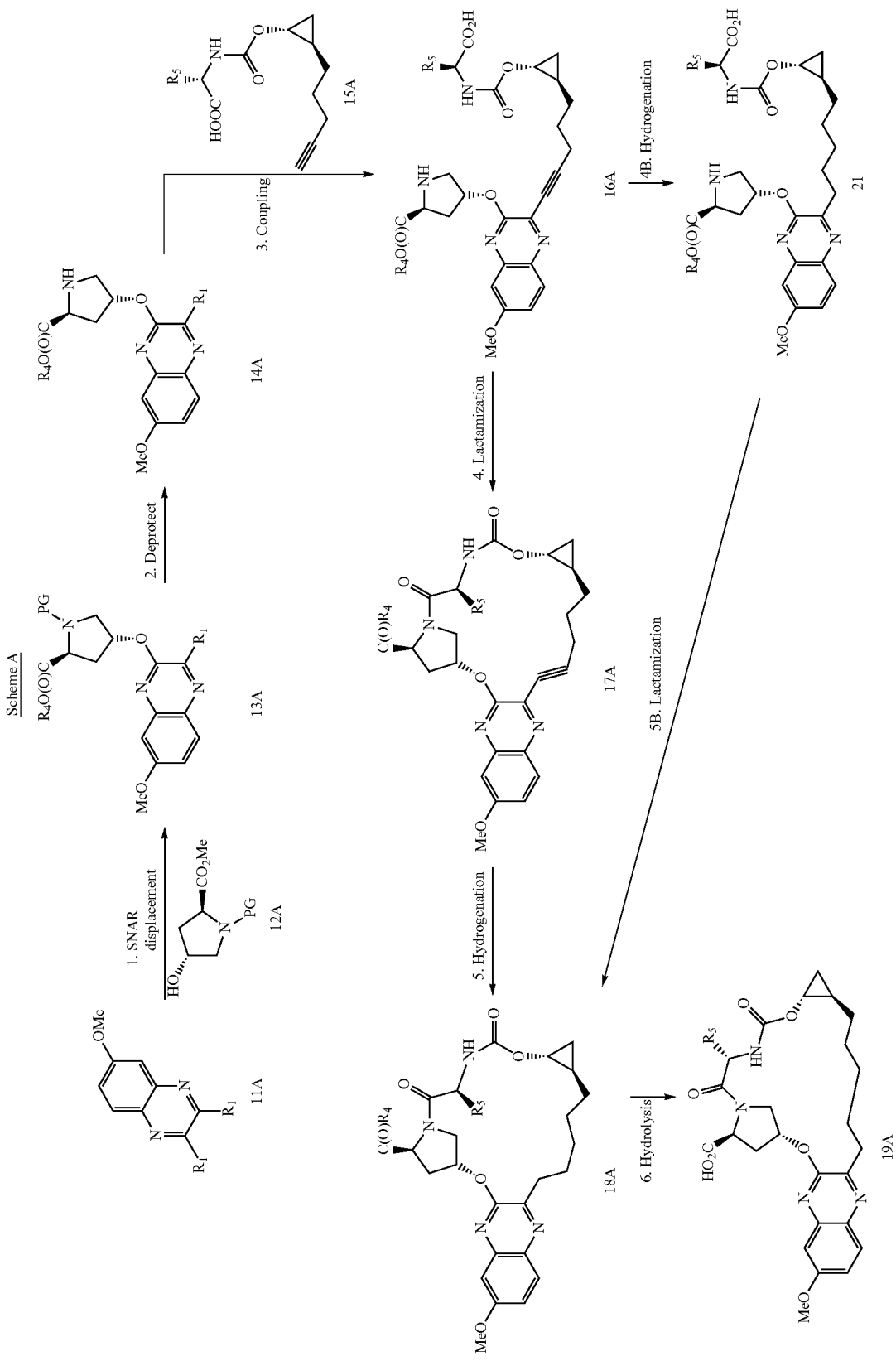

The compounds illustrated in Scheme A are in the neutral form. It should be understood that different embodiments described throughout the application include appropriate acid or base forms of the different compounds.

"PG" refers to a protecting group. In different embodiments described throughout the application where a protecting group is employed: PG is an acid-labile carbomate; PG is BOC, Fmoc, 9-Anthrylmethyl, Msz, Moz, or Cbz; or PG is Boc.

each $R_1$ is a leaving group as described for Formula below, including different embodiments.

$R_4$ is as described for Formula I, including different embodiments as provided below.

$R_5$ is as described for Structure I, including different embodiments as provided below.

A preferred overall scheme is illustrated in scheme B. Further aspects and embodiments of Scheme B are directed to each of the different steps, alone or in any combination with up stream or downstream steps.

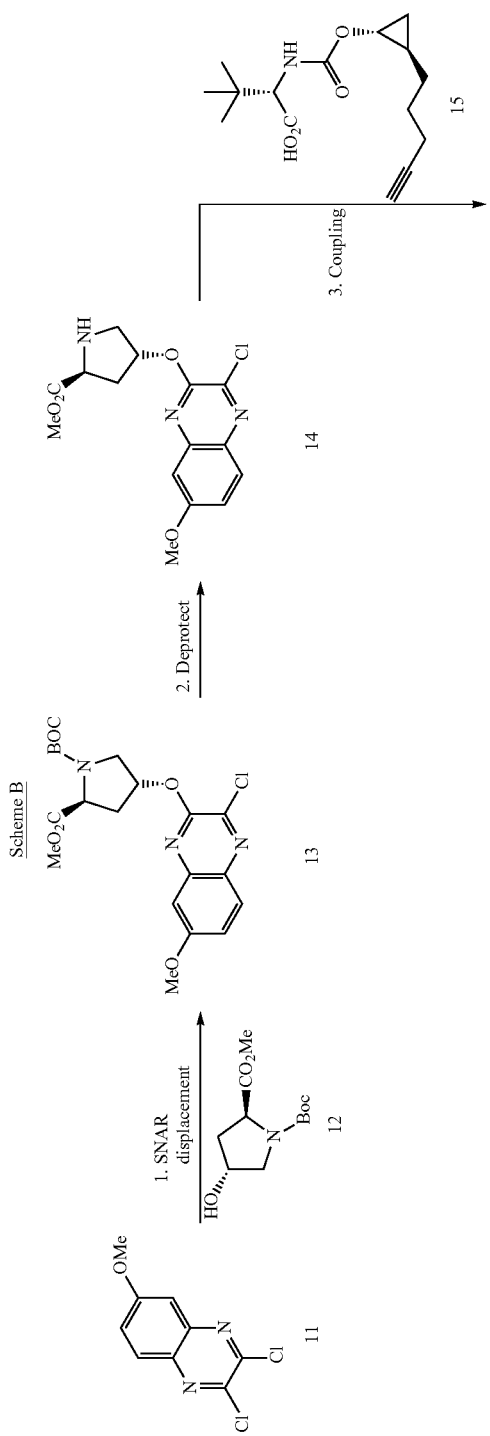

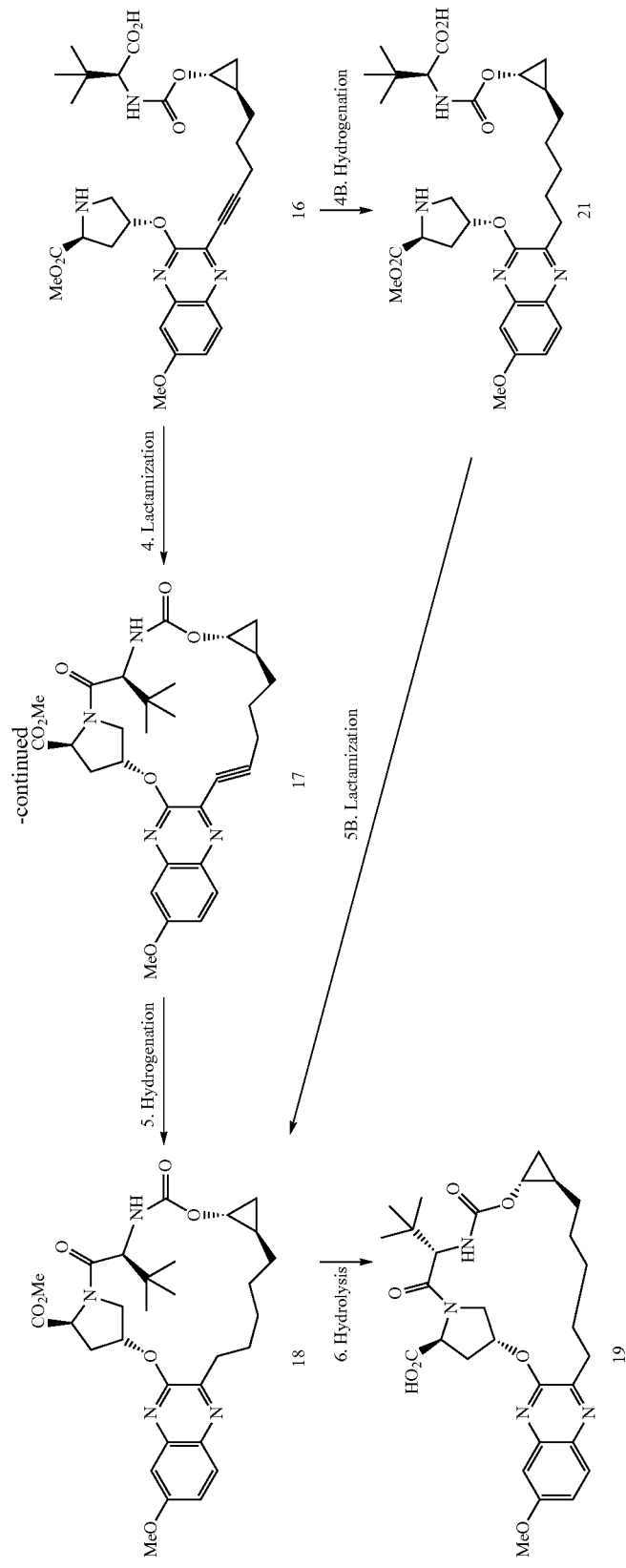

An aspect of the invention is directed to a compound Formula I or a salt thereof:

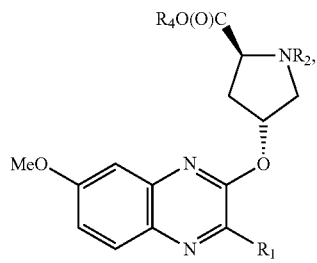
(Formula I)

wherein $R_1$ is a leaving group, or

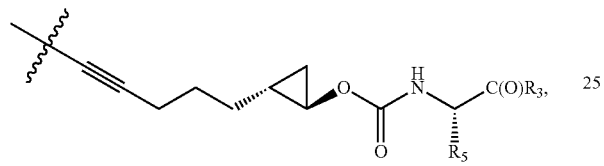
(Structure I)

provided that if $R_1$ is a leaving group, then $R_2$ is H; and if $R_1$ is Structure I, then $R_2$ is H and $R_3$ is OH, or $R_2$ and $R_3$ are joined together as a covalent bond;

$R_4$ is either $C_{1-6}$ alkyl or aryl; and $R_5$ is either a $C_{1-8}$ alkyl or $C_{3-8}$ cycloalkyl.

In a first embodiment the $R_1$ leaving group is a halogen, mesylate, tosylate or $CF_3SO_3$.

In a second embodiment the $R_1$ leaving group is a halogen.

In a third embodiment the $R_1$ leaving group is a Cl.

In a fourth embodiment $R_1$ is Structure I.

In a fifth embodiment $R_4$ is $C_{1-6}$ alkyl and $R_1$ is as provided in the Formula I or embodiments 1-4.

In a sixth embodiment $R_4$ is methyl and $R_1$ is as provided in the Formula I or embodiments 1-4.

In a seventh embodiment $R_5$ is t-butyl and the other variables are as provided in the Formula I or embodiments 1-6.

In an eighth embodiment $R_5$ is cyclohexyl and the other variables are as provided in the Formula I or embodiments 1-6.

In a ninth embodiment the compound is either:

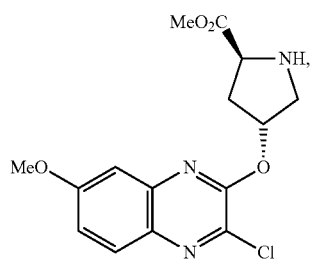
(Compound 14)

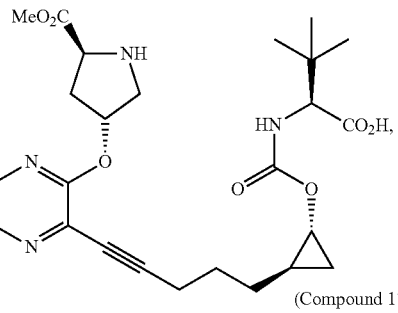
(Compound 16)

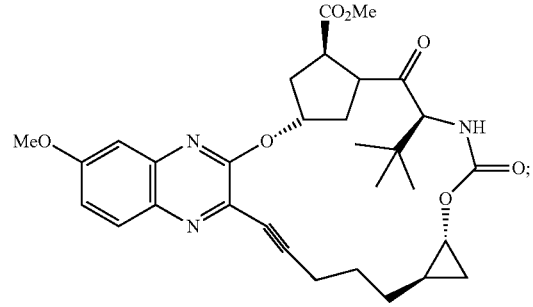
(Compound 17)

or a salt thereof.

In a tenth embodiment, Compound 14 is a methylsulfonic acid salt and/or a MeCN solvate.

A first aspect is directed to a method of making Compound 16A

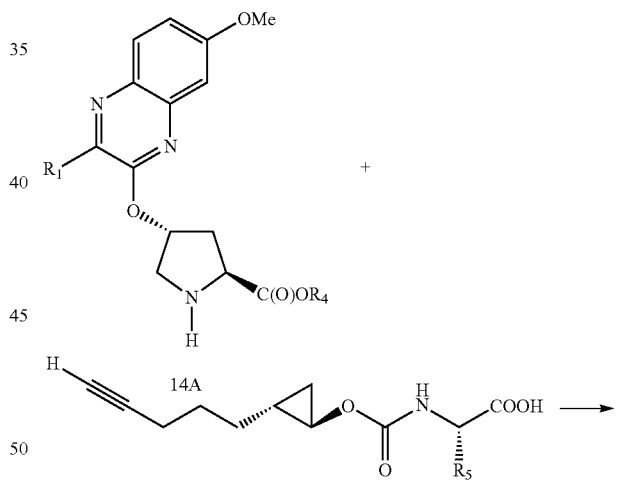

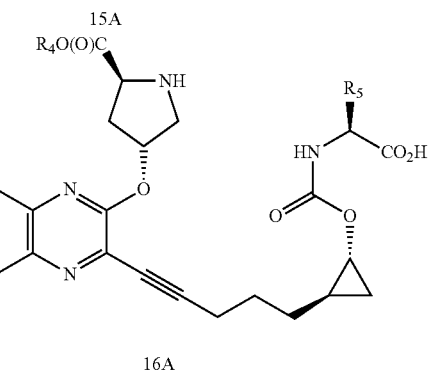
15A

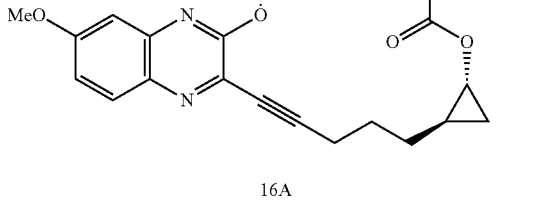
16A wherein Compound 14A, 15A, and 16A may be provided as a salt. Reference to different compounds in a reaction possibly (e.g., may be) being provided as a salt indicates that any one compound, any combination of compounds, or all of the compounds may be provided as a salt;

$R_1$ is a leaving group as described above in the aspects and embodiments directed to a compound of Formula I or a salt thereof; and $R_4$ and $R_5$ are as described above in the aspects and embodiments directed to a compound of Formula I or a salt thereof.

In a further embodiment Compound 16 is made by a method comprising the step of:

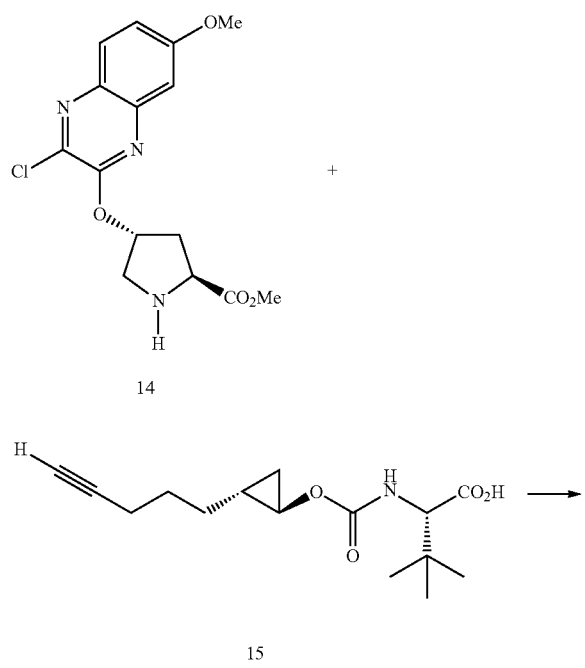

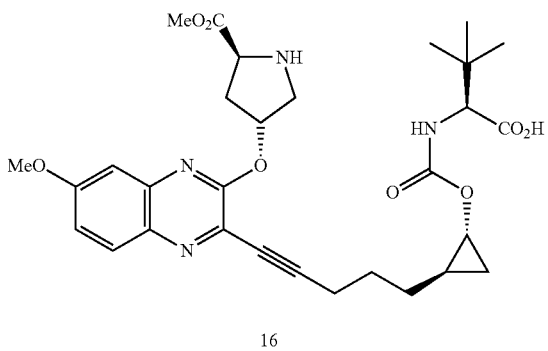

16 wherein Compounds 14, 15, and 16 may be provided as a salt.

In different embodiments concerning the compounds used in the reaction, Compound 14 is a methylsulfonic acid salt, Compound 14 is a MeCN solvate of a methylsulfonic acid salt, and/or Compound 15 is a TBA salt or DBA salt.

In embodiments concerning the reaction conditions for making 16A or Compound 16, Sonogashira cross coupling using a suitable catalyst is carried out. Suitable catalysts include a combination of copper halide with palladium salts. In different embodiments, the catalyst is Copper(I) iodide, Copper(I) bromide, Copper(I) chloride, or Copper (I) cyanide. The use of a combination of Copper(I) iodide and bis(triphenylphosphine)palladium(II) dichloride in the presence of an amine base is preferred.

Suitable solvents include alcohols, THF, or MeCN. Examples of alcohols that can be used include methanol, ethanol, propanol and isopropanol.

Preferred amine bases are triethyl amine, tributyl amine, Hunig's base, t-butylamine, and diisopropylamine.

A preferred general temperature range is ~20-80° C., more preferable the temperature is about 30-50° C., or further specified to 35° C.

In a further embodiment, Compound 17 or 17A is formed by lactamization of compound 16 or 16A. Lacatamization can be carried out using techniques described herein.

A second aspect is directed to a method of making Compound 17 comprising:

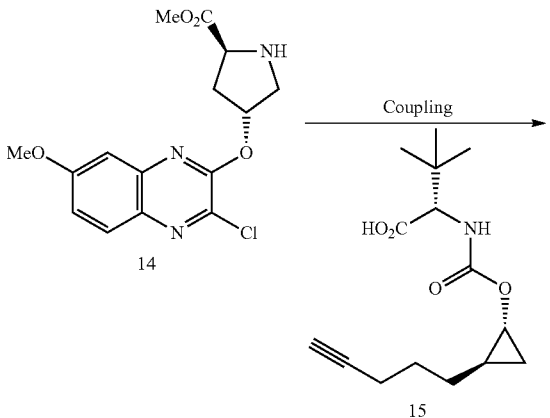

-continued

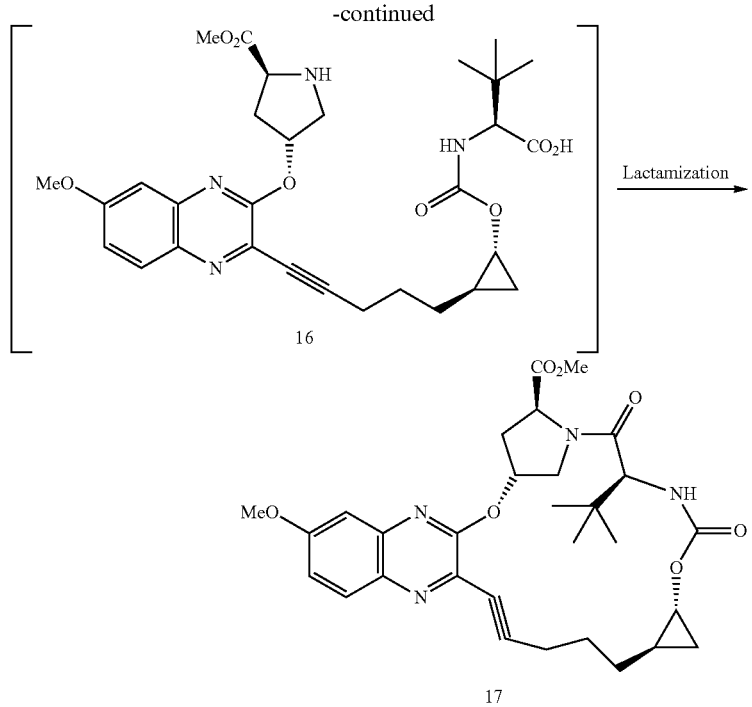

wherein compound 14, 15, 16, and 17 may be provided as a salt, and Compound 16 is not isolated prior to lactamization.

Different embodiments concerning coupling are as provided above in the embodiments concerning making Compound 16.

Intermediate Compound 16 does not need to be isolated, and can be used directly as a crude stream after aqueous workup. It is better to control the water content in the reaction mixture to minimize the formation of by-products and to improve the yield. The KF spec is preferably KF<2000 ppm, preferably <500 ppm. In different embodiments the reaction is carried out at −10 to 50° C., preferably at 0° C.; and Compound 16 is added slowly, preferably over 10 hours.

Suitable solvents include DMAc, DMF, NMP, methylenechloride, IPAc, EtOAc, and THF. DMAc is preferred. Various lactamization coupling reagents can be used, such as HATU, EDC, EDC-HOBT, EDC-pyridine, EDC-HOAT, EDC-HOPO, CIP, EDC-HOSu, EDC-PFP, T3P, and HATU/EDC variants The use of HATU is preferred.

A third aspect is a directed to a method of making Compound 18 or salt thereof comprising the step of hydrogenation of Compound 17 or salt thereof. Suitable conditions include the use of a palladium catalyst and a solvent. Examples of solvents include THF, Me-THF, methyl cyclopentyl ether, EtOAc, IPAc, MeOH, EtOH, propanol, isopropanol, DMAc.

THF is a preferred solvent. A general temperature range is temperature from 0-40° C., preferably 15-25° C.

A fourth aspect is directed to a method of making Compound 19 or salt thereof comprising the step of hydrolyzing Compound 18 or a salt thereof. Suitable conditions include the use of bases such as NaOH, LiOH and KOH in aqueous solvents such as MeTHF, THF, MeOH, EtOH, IPA and n-propyl alcohol. A general temperature range is 0-80° C., preferably 40-50° C. In an embodiment, Compound 19 is provided as a hydrate.

A fifth aspect is directed to a method of making Compound 18 comprising:

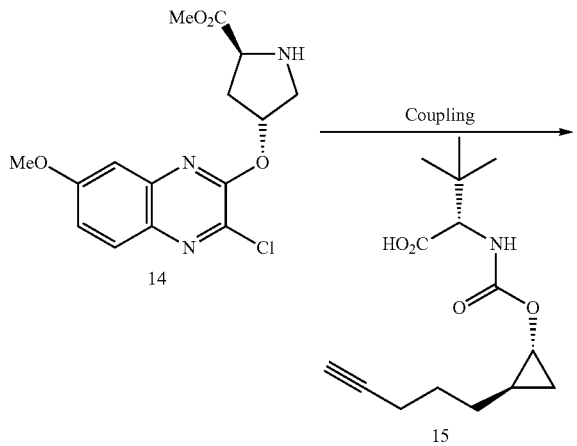

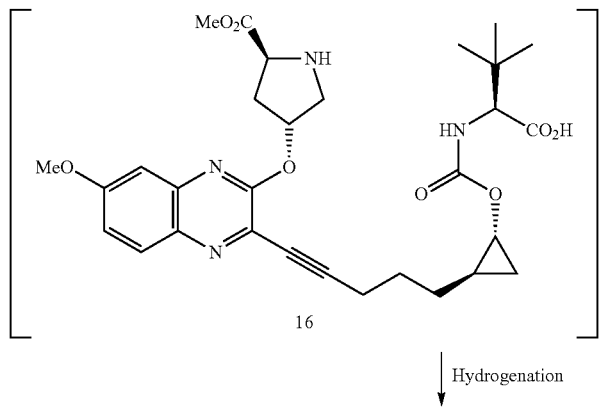

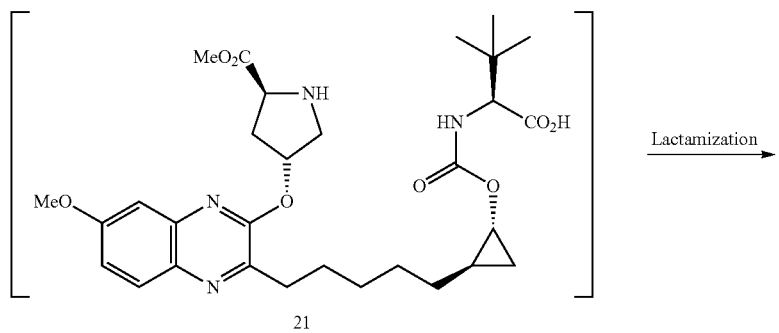

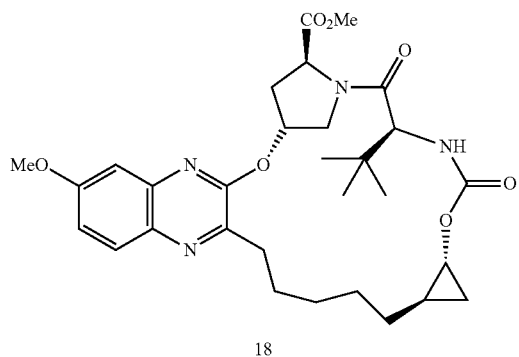

wherein compounds 14, 15, 16, 21, and 18 may be provided as salts, and Compound 16 and 21 are not isolated.

Examples of suitable hydrogenation conditions are as described for hydrogenating Compound 17 above.

Examples of suitable lactamization conditions are as described for lactamization of Compound 16 above.

A sixth aspect is direct to a method of making Compound 14 comprising the steps:

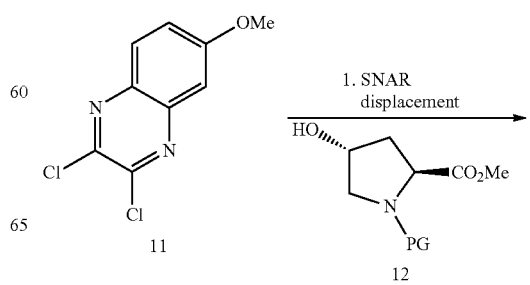

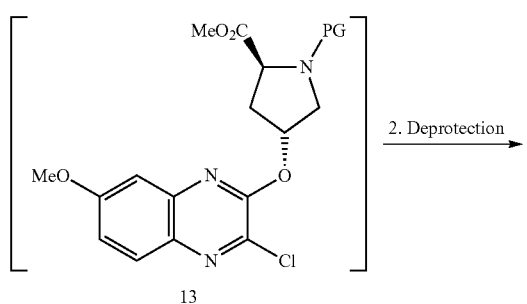

13

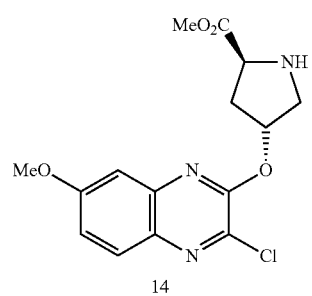

14

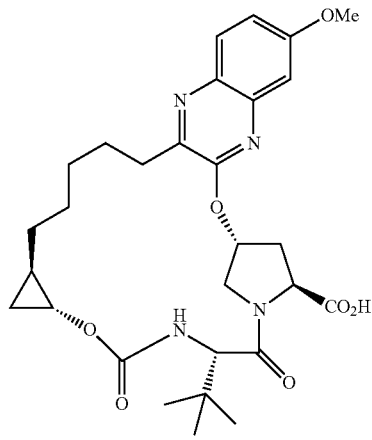

Compound 19 or salt thereof, to

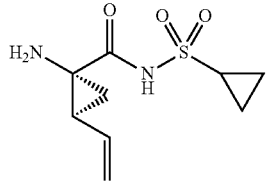

Compound 20 or salt thereof, to form Compound A or salt thereof, wherein the coupling comprises the use of a coupling reagent and pyridine or a pyridine derivative.

Preferably, no detectable HOBt is present. The reaction can be carried out using a coupling reagent, an aprotic organic solvent and pyridine or a pyridine derivative. A general temperature is −10° C. to 50° C. (preferably 0 to 20° C.). Examples of coupling reagents include dicyclohexylcarbodiimide (DCC), N,N'-diisopropylcarbodiimide (DIC), and 1-ethyl-3-(3-dimethylaminopropyl) carbodiimide (EDC), and HATU. Examples of aprotic organic solvents include acetonitrile, THF, THF-DMAc, THF-DMF, THF-NMP, and toluene. In an embodiment, THF-DMAc or THF is used.

In different embodiments EDC is used; EDC is used along pyridine and acetonitrile; EDC is used along with at least 10 equivalents of pyridine and acetonitrile; and EDC is used along with pyridine and THF-DMAc.

In an embodiment, directed to using EDC with THF-DMAc, Compound 19 hydrate is azeotropically dried in THF, and combined with Compound 20 and DMAc, followed by addition of pyridine or a pyridine derivative and EDC. A preferred temperature range is from about 0° C. to 20° C., preferably at 0-5° C. for 1 hour followed by 15-20° C. for additional 1-2 hours. The use of reaction conditions employing THF-DMAc or THF in conjunction with EDC facilitates control of the reaction profile and suppression of the formation of by-products, for example, by reducing the over reaction of coupling agent. Alternative procedures could result in significant over reaction of coupling agent with compound A in the absence of quenching.

In an embodiment, Compound 20 used in this aspect, including any of the embodiments, is pTSA salt.

Preferred pyridine derivatives have electron donating or neutral groups at the 3 and 4 position. Examples of general structures covering pyridine and derivatives include:

wherein compound 11, 12, 13 and 14 may be provided as a salt, and Compound 13 is not isolated.

The reaction can be carried out by SNAR replacement of Compound 11 with Compound 12 in the presence of a base. Compound 11 is described by Sarges et al., *J. Med. Chem.* 33:2240-2254, 1990. A general temperature for the reaction is 20-100° C., with a preferred temperature being 40-45° C. A wide range of solvents can be using including aprotic polar solvents, DMF, DMAc, NMP, DMSO, and DMPU. A preferred solvent is DMAc. Different bases can be used including $Cs_2CO_3$, DBU, $K_2CO_3$, $K_3PO_4$, and KOtBu. A preferred base is DBU. An advantage of the reaction was high regioselectivity and no detected isomerization of the hydroxyproline.

Deprotection can be carried out with various acids including pTSA, $PhSO_3H$, $MeSO_3H$, HCl, $H_2SO_4$, HBr, AcOH—HCl in a wide range solvents including IPAc, EtOAc, MeCN, and DMAc. The use of methansulfonic acid in MeCN is preferred allowing direct isolation of Compound 14 as a MeCN solvate $MeSO_3H$ salt from the reaction mixture. A general temperature for the reaction is 0-80° C., with a preferred temperature being ~40° C.

Examples of combinations of upstream and downstream steps include methods comprising: Aspects 1, 3, 4 and 6; Aspects 2, 3, 4 and 6; Aspects 4, 5 and 6; and subsets within these combinations. Methods directed to subsets comprising adjacent steps, or a series of adjacent steps. For examples, subsets within the combination of Aspects 1, 3, 4 and 6, include a method comprising 1 and 3; 1, 3, and 4; 1, 3, 4, and 6; 6 and 1; 3 and 4; and so forth.

Compound A

Another aspect is directed to method of making Compound A comprising the step of coupling:

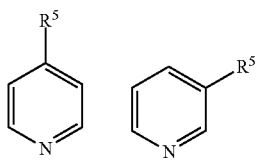

wherein R[5] is either hydrogen, aryl, halogen, $C_{1-6}$ alkyl, O—$C_{1-6}$ alkyl or $C_3$-$C_8$ cycloalkyl. Preferred reagents are pyridine, 4-phenylpyridine, 4-alkylpyridine, methylpyridine, 3- or 4-mono or dialkylpyridine, wherein the alkyl group can be a $C_{1-6}$ alkyl.

Compounds

The term "alkyl" refers to a monovalent straight or branched chain, saturated aliphatic hydrocarbon radical having a number of carbon atoms in the specified range. Thus, for example, "$C_{1-6}$ alkyl" refers to any of the hexyl alkyl and pentyl alkyl isomers as well as n-, iso-, sec- and t-butyl, n- and iso-propyl, ethyl, and methyl. As another example, "$C_{1-4}$ alkyl" refers to n-, iso-, sec- and t-butyl, n- and isopropyl, ethyl, and methyl.

The term "cycloalkyl" refers to any monocyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

An "aryl" is either phenyl, substituted phenyl, naphthyl, substituted naphthyl, heteroaryl, or substituted heteroaryl, provided that substituted phenyl, substituted naphthyl, and substituted heteroaryl, each have 1 to 5 substituents independently selected from the group consisting of:

(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^C)R^D$, $C(O)N(R^C)R^D$, $C(O)R^C$, $CO_2R^C$, $SR^C$, $S(O)R^C$, $SO_2R^C$, $SO_2N(R^C)R^D$, $N(R^C)C(O)R^D$, $N(R^C)CO_2R^D$, $N(R^C)SO_2R^D$, $N(R^C)SO_2N(R^C)R^D$, $OC(O)N(R^C)R^D$, $N(R^C)C(O)N(R^C)R^D$, or $N(R^C)C(O)C(O)N(R^C)R^D$,
(3) O—$C_{1-6}$ alkyl,
(4) $C_{1-6}$ haloalkyl,
(5) O—$C_{1-6}$ haloalkyl,
(6) OH,
(7) halogen,
(8) CN,
(9) $NO_2$,
(10) $N(R^C)R^D$,
(11) $C(O)N(R^C)R^D$,
(12) $C(O)R^C$,
(13) $C(O)$—$C_{1-6}$ haloalkyl,
(14) $C(O)OR^C$,
(15) $OC(O)N(R_C)R^D$,
(16) $SR^C$,
(17) $S(O)R^C$,
(18) $SO_2R^C$,
(19) $SO_2N(R^C)R^D$,
(20) $N(R^C)SO_2R^D$,
(21) $N(R^C)SO_2N(R^C)R^D$,
(22) $N(R^C)C(O)R^D$,
(23) $N(R^C)C(O)N(R^C)R^D$,
(24) $N(R^C)C(O)C(O)N(R^C)R^D$, or
(25) $N(R^C)CO_2R^D$; and $R^C$ and $R^D$ are each independently H or $C_{1-6}$, alkyl.

A "heteroaryl" is a (i) a 5- or 6-membered heteroaromatic ring containing from 1 to 4 heteroatoms independently selected from N, O and S or (ii) a 9- or 10-membered bicyclic, fused ring system containing from 1 to 4 heteroatoms independently selected from N, O and S.

The atoms in a compound described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

Isotopically-enriched compounds described herein can be prepared without undue experimentation by conventional techniques well known to those skilled in the art or by processes analogous to those described in the Schemes and Examples provided herein using appropriate isotopically-enriched reagents and/or intermediates.

Compounds described herein having appropriate functional groups can be provided as salts. Examples of such compounds are described herein by reference to possible salts. Such reference is for illustration purposes, and additional embodiments include salts of any compound described herein having suitable groups.

Pharmaceutically acceptable salts can be used with compounds for treating patients. Non-pharmaceutical salts may, however, be useful in the preparation of intermediate compounds.

Pharmaceutically acceptable salts are suitable for administration to a patient, preferably, a human. Suitable salts include acid addition salts which may, for example, be formed by mixing a solution of a compound with a solution of a pharmaceutically acceptable acid such as hydrochloric acid, sulfuric acid, acetic acid, trifluoroacetic acid, or benzoic acid. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Intermediate Forms

A first embodiment is directed to Compound 19 hydrate I, where the hydrate is characterized by an X-ray powder diffraction pattern obtained using copper $K_\alpha$ radiation (i.e., the radiation source is a combination of Cu $K_{\alpha 1}$ and $K_{\alpha 2}$ radiation), which comprises three or more characteristic peaks. Characteristic peeks are illustrated in FIG. 1.

A second embodiment is directed to Compound 19 hydrate I, where the hydrate is characterized by an X-ray powder diffraction pattern obtained using copper $K_\alpha$ radiation which comprises 2Θ values in degrees of about 8.7, 22.2, and 23.5.

Reference to "about" with respect to 2Θ values provided herein indicates ±0.1.

A third embodiment is directed to Compound 19 hydrate I, where the hydrate is characterized by an X-ray powder diffraction pattern obtained using copper $K_\alpha$ radiation which comprises 2Θ values (i.e., reflections at 2Θ values) in degrees of about 8.7, 22.2, 23.5, 8.3, 14.7, 7.6, 22.8, and 11.3.

Figure 2:
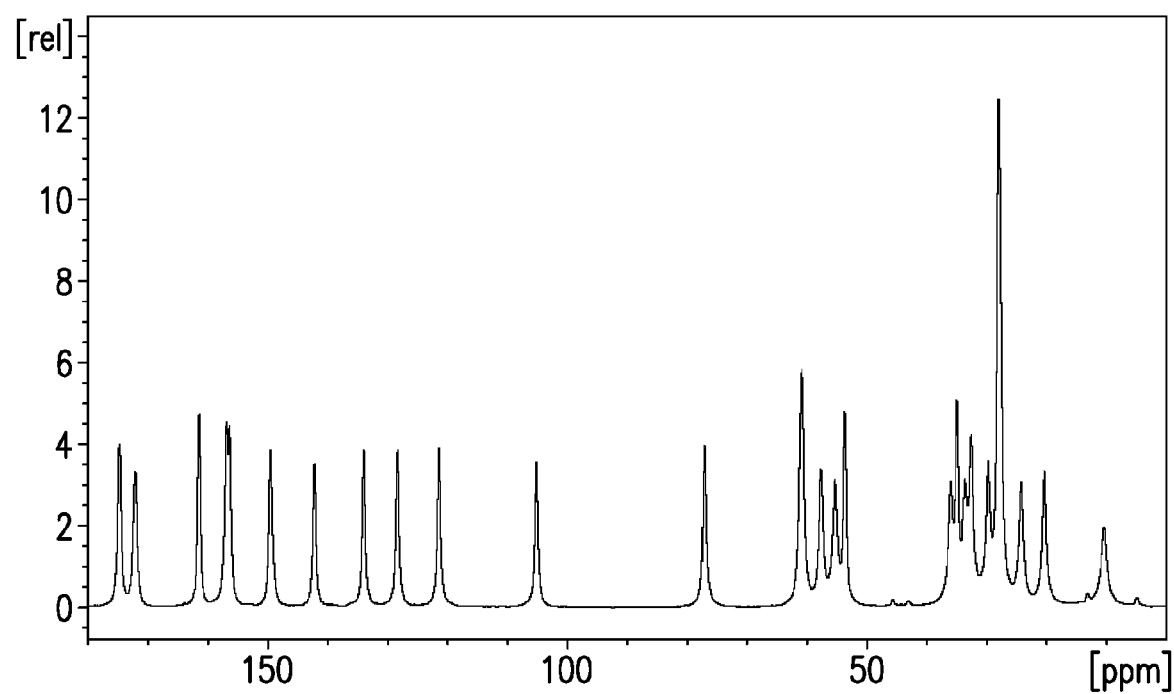
FIG. 2 illustrates a solid state C-13 CPMAS NMR for Compound 19 hydrate 1.

A fourth embodiment is directed to Compound 19 hydrate I, where the hydrate is characterized by a solid state carbon-13 CPMAS NMR spectrum provided in FIG. 2.

A fourth embodiment is directed to Compound 19 hydrate 1, where the hydrate is characterized by a solid state carbon-13 CPMAS NMR comprising peaks at about 174.7, 172.0, 161.4, 156.8, 156.3, 149.5, 142.1, 133.9, 128.2, 121.3, 105.0, 76.9, 60.7, 57.5, 55.1, 53.5, 35.8, 34.7, 33.4, 32.4, 29.5, 27.8, 24.0, and 20.2 ppm.

Reference to "about" with respect to the solid state carbon-13 CPMAS NMR 2Θ values provided herein indicates ±0.1.

Figure 3:
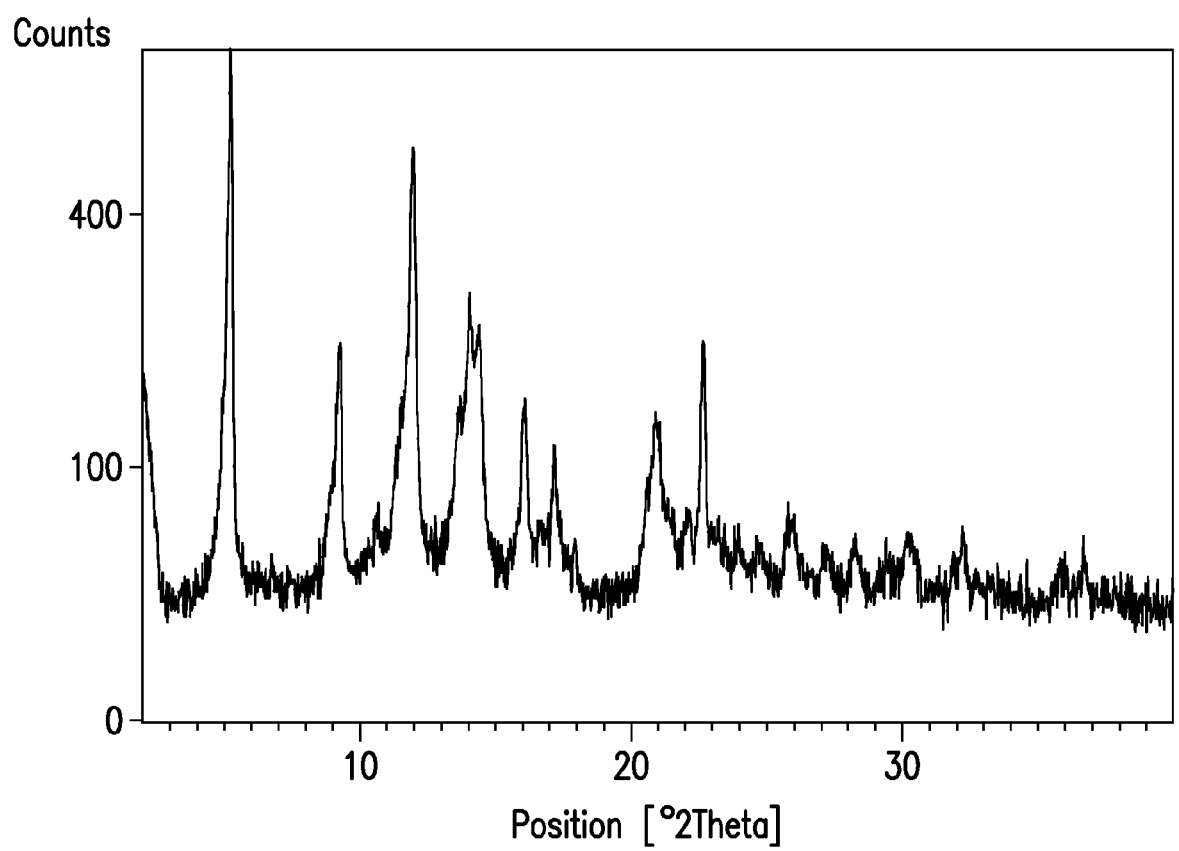
FIG. 3 illustrates an X-ray diffraction pattern for a MeCN solvate of a Compound 14 methylsulfonic acid salt.

A fifth embodiment is directed to a MeCN solvate of a Compound 14 methylsulfonic acid salt, where the solvate is characterized by an X-ray powder diffraction pattern obtained using copper $K_\alpha$ radiation which comprises three or more characteristic peaks. Characteristic peeks are illustrated in FIG. 3.

A sixth embodiment is directed to a MeCN solvate of a Compound 14 methylsulfonic acid salt, where the solvate is characterized by an X-ray powder diffraction pattern obtained using copper Kα radiation which comprises 2Θ values in degrees of about 5.3, 12.0, and 14.1.

A seventh embodiment is directed to a MeCN solvate of a Compound 14 methylsulfonic acid salt, where the solvate is characterized by an X-ray powder diffraction pattern obtained using copper Kα radiation which comprises 2Θ values in degrees of about 5.3, 12.0, 14.1, 22.7, 9.3, 16.1, 20.9, 17.2, 25.8, and 32.3.

Administration and Compositions

Compounds described herein having therapeutic applications, such as Compound A, can be administered to a patient infected with HCV. The term "administration" and variants thereof (e.g., "administering" a compound) means providing the compound to the individual in need of treatment. When a compound is provided in combination with one or more other active agents (e.g., antiviral agents useful for treating HCV infection), "administration" and its variants are each understood to include concurrent and sequential provision of the compound or salt and other agents.

As used herein, the term "composition" is intended to encompass a product comprising the specified ingredients, as well as any product which results, directly or indirectly, from combining the specified ingredients.

By "pharmaceutically acceptable" is meant the ingredients of the pharmaceutical composition are compatible with each other and are suitable to the recipient thereof.

The term "subject" (alternatively referred to herein as "patient") as used herein refers to an animal, preferably a mammal, most preferably a human, who is the object of treatment, observation or experiment.

The term "effective amount" indicates a sufficient amount to exert a therapeutic or prophylactic effect. For a patient infected with HCV, an effective amount is sufficient to achieve one or more of the following effects: reduce the ability of HCV to replicate, reduce HCV load, and increase viral clearance. For a patient not infected with HCV, an effective amount is sufficient to achieve one or more of the following: a reduced susceptibility to HCV infection, and a reduced ability of the infecting virus to establish persistent infection for chronic disease.

For the purpose of inhibiting HCV NS3 protease and treating HCV infection and/or reducing the likelihood or severity of symptoms of HCV infection, the compounds, optionally in the form of a salt, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

Compounds can, for example, be administered by one or more of the following routes: oral, parenteral (including subcutaneous injections, intravenous, intramuscular, intrasternal injection or infusion techniques), by inhalation (such as in a spray form), or rectal, in the form of a unit dosage of a pharmaceutical composition containing an effective amount of the compound and pharmaceutically-acceptable carrier (e.g., a carrier suitable for administration to a human patient), adjuvants and vehicles. Liquid preparations suitable for oral administration (e.g., suspensions, syrups, elixirs and the like) can employ media such as water, glycols, oils, alcohols and the like. Solid preparations suitable for oral administration (e.g., powders, pills, capsules and tablets) can employ solid excipients as such starches, sugars, kaolin, lubricants, binders, disintegrating agents and the like. Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in *Remington: The Science and Practice of Pharmacy*, $21^{th}$ edition (Lippincott Williams & Wilkins, 2006).

Therapeutic compounds can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

HCV Inhibitory Activity

The ability of a compound to inhibit HCV NS3 activity, HCV replicon activity, and HCV replication activity can be evaluated using techniques well-known in the art. (See, for example, Carroll et al., *J. Biol. Chem.* 278:11979-11984, 2003.)

One such assay is a HCV NS3 protease time-resolved fluorescence (TRF) assay as described below and in Mao et al., *Anal. Biochem.* 373:1-8, 2008 and Mao et al., WO 2006/102087. A NS3 protease assay can be performed, for example, in a final volume of 100 μl assay buffer containing 50 mM HEPES, pH 7.5, 150 mM NaCl, 15% glycerol, 0.15% TRITON X-100, 10 mM DTT, and 0.1% PEG 8000. NS3 and NS4A are pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 μl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 μs delay. Testing concentrations of different enzyme forms are selected to result in a signal to background ratio (S/B) of 10-30. $IC_{50}$ values are derived using a standard four-parameter fit to the data. $K_i$ values are derived from $IC_{50}$ values using the following formula, $$IC_{50}=K_i(1+[S]/K_M), \quad \text{Eqn (1)},$$

where [S] is the concentration of substrate peptide in the reaction and $K_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996); and Mao et al., *Analytical Biochemistry* 373: 1-8, (2008).

Abbreviations
BOC: t-Butoxycarbonyl
Cbz: Benzyloxycarbonyl
CDI: 1,1'-Carbonyldiimidazole
CIP: 2-Chloro-1-methylpyridinium iodide
CPME: Cyclopentyl methyl ether
DABO: 1,4-Diazabicyclo[2.2.2.]octane
DBA saltdibenzylamine
DBU: 1,8-Diazobicyclo[5.4.0]undec-7-ene
DCC: N,N'-Dicyclohexylcarbodiimide
DIC: N,N'-diisopropylcarbodiimide
DIPEA: Diisopropylethylamine
DMAc: N,N-Dimethylacetamide
DMF: N,N-Dimethylformamide
DMPU: N,N-dimethylpropyleneurea
DMSO: Dimethylsulfoxide
EDC: 1-Ethyl-3-(3-dimethylaminopropyl) carbodiimide
EtOAc: Ethyl acetate
Fmoc: 9-Fluorenylmethyloxycarbonyl
HATU: 2-(1H-7-Azabenzotriazole-1-yl)-1,1,3,3-tetramethyluronium hexafluorophosphate
HOAT: 1-Hydroxy-7-azabenzotriazole
HOBT: 1-Hydroxybenzotriazole
HOPO: 2-Hydroxypyridine-N-oxide
HOSu: N-hydroxysuccinimide
IPA: Isopropanol
IPAc: Isopropyl acetate
MTBE: t-butyl methyl ether
MsOH and MSA: $CH_3SO_3H$ or methanesulfonic acid
Moz: p-Methoxybenzyloxycarbonyl
Msz: 4-Methylsulfinylbenzyloxycarbonyl
NMP: N-Methylpyrrolidone
PFP: pentafluorophenol
T3P: propylphosphonic anhydride
TBA: t-butyl amine
TEA: Triethylamine
THF: Tetrahydrofuran
pTSA and TsOH are each abbreviations for p-toluenesulfonic acid.

EXAMPLES

The examples provided below are intended to illustrate the invention and its practice. Unless otherwise provided in the claims, the examples are not to be construed as limitations on the scope or spirit of the invention.

Example 1

Preparation of 2-[2-(3-Chloro-propyl)-cyclopropyl]-4,4,5,5-tetramethyl-[1,3,2]dioxaborolane (Compound 3)

Compound 2 can be prepared as described by Shirakawa et al. *Synthesis* 11:1814-1820, 2004.)

Compound 3 was produced as follows: To a 5 L flask equipped with a nitrogen inlet, mechanical stirrer, dropping funnel and thermocouple under $N_2$ was added 800 mL dichloromethane and 800 mL of a 1 M diethylzinc solution in heptane (0.8 mol, 1.07 equiv). The solution was cooled with an ice bath to an internal temperature of 3° C. To the flask was then added from the dropping funnel a solution of 57.6 mL trifluoroacetic acid (0.748 mol, 1.0 equiv) in 200 mL dichloromethane over 1 hour, keeping the internal temperature below 10° C. The resulting suspension was stirred for 30 min at 3° C. To the flask was then added 72.4 mL diiodomethane (0.897 mol, 1.2 equiv) in a single portion. After stirring at 3° C. for 30 min, 172 mL of 2 (0.748 mol, 1.0 equiv) was added to the solution in a single portion. The flask was then allowed to warm to room temperature and a white precipitate began to form. After 3 hours, GC analysis indicated the reaction was at 90% conversion. The suspension was aged for an additional 17 hours or until complete consumption of 2 is observed. At that point, 800 mL of 1 M HCl (0.8 mol, 1.07 equiv) was added and a +5 exotherm was observed. The biphasic mixture was stirred for 30 min to dissolve the precipitated solids and the organic layer was separated. Extraction of the aqueous layer with 200 mL dichloromethane, washing of the combined organic layers with 500 mL brine and concentration in vacuo gave 194 g of 3 as a yellow oil (74 wt % in DCM). $^1$H NMR (400 MHz, $CDCl_3$) δ 3.59 (t, 2H, J=6.7 Hz), 1.90 (pent, 2H, J=7.1 Hz), 1.49 (sext, 1H, J=7.0 Hz), 1.36 (sext, 1H, J=7.0 Hz), 1.23 (s, 12H), 0.93 (m, 1H), 0.71 (m, 1H), 0.44 (m, 1H), −0.35 (dt, 1H, J=9.4, 5.7 Hz); $^{13}$C NMR (100 MHz, $CDCl_3$) δ 82.82, 44.74, 32.67, 32.22, 24.64, 17.22, 11.24, 0.5 (bs); GC: HP1 (30 m×0.32 mm; 0.25 μm), 25 psi, 200° C.

front inlet. 5 min @ 50° C., ramp 25° C./min to 250° C. then hold for 4 min, t$_r$(2)=9.78 min, t$_r$(3)=10.08 min.

Example 2

Preparation of 2-(3-Chloro-propyl)-cyclopropanol (Compound 4)

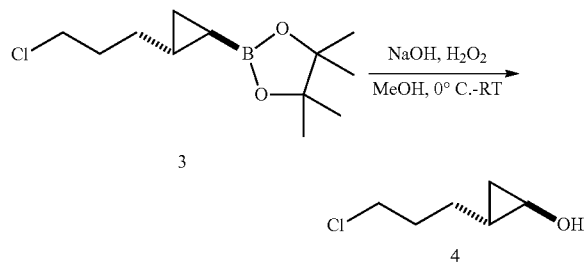

To a 3 L flask equipped with a nitrogen inlet, mechanical stirrer, dropping funnel and thermocouple was added 143 g of 3 (0.585 mol, 1.0 equiv) in 1 L methanol. To the flask was then added from the dropping funnel 58.5 mL of 10 M sodium hydroxide (0.585 mol, 1.0 equiv) over 30 min, while the internal temperature was maintained below 10° C. with external cooling. After stirring for 30 min, 120 mL of 30 wt % hydrogen peroxide solution (1.17 mol, 2 equiv) was slowly added from the dropping funnel over 1 hour, keeping the internal temperature below 10° C. Upon completion of the addition, the resulting colorless slurry was then stirred at ambient temperature for 30 min or until complete consumption of 3 was observed by GC. 2 M HCl (375 mL) was added from the dropping funnel over 30 min, keeping the internal temperature below 10° C. To this clear yellow solution was then slowly added 500 mL of a 1 M solution of Na$_2$SO$_3$ from the dropping funnel, keeping the internal temperature below 10° C. The resulting suspension was then filtered and extracted 3×200 mL MTBE. Concentration followed by silica gel column chromatography (6:4 hexane:ethyl acetate), to remove pinacol, gave 60.6 g of product 4 as a clear oil (90 wt %). $^1$H NMR (400 MHz, CDCl$_3$) δ 3.62 (t, 2H, J=6.6 Hz), 3.27 (dt, 1H, J=6.3, 2.6 Hz), 1.89 (pent, 2H, J=6.8 Hz), 1.85 (bs, OH), 1.43 (sext, 1H, J=7.0 Hz), 1.28 (sext, 1H, J=7.0 Hz), 0.94 (m, 1H), 0.75 (m, 1H), 0.38 (q, 1H, J=6.0 Hz); $^{13}$C NMR (100 MHz, CDCl$_3$) δ 52.21, 44.69, 31.91, 28.69, 19.69, 14.15; GC: HP1 (30 m×0.32 mm; 0.25 µm), 25 psi, 200° C. front inlet. 5 min @ 50° C., ramp 25° C./min to 250° C. then hold for 4 min, t$_r$(3)=10.08 min, t$_r$(4)=7.15 min.

Example 3

Preparation of 2-Pent-4-ynyl-cyclopropanol (rac-Compound 5)

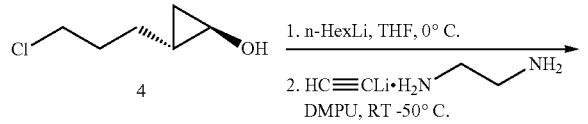

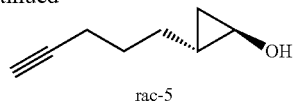

To a 2-neck 15-mL flask equipped with a temperature probe, N$_2$ inlet, and septum was added 1 g of 4 (7.28 mmol, 1.0 equiv) and 3.0 mL THF. The solution was cooled to an internal temperature of 0° C. with an ice bath. To this solution was added 2.95 mL of 33 wt % n-Hexyllithium (7.28 mmol, 1.0 equiv) slowly via syringe pump over 1 hour. Internal temperature rose to 6.8° C. and solution became yellow. In a separate 3-neck 100-mL flask equipped with a temperature probe, N$_2$ inlet, and septum 0.82 g of lithium acetylide-ethylenediamine complex (8.01 mmol, 1.1 equiv) was slurried in 5.0 mL of DMPU at room temperature. To this room temperature slurry, the cold solution of the deprotonated cyclopropanol was transferred via cannula over 5 min. After the addition, the brown mixture was heated to an internal temperature of 52° C. with a heating mantle for 3 hours or until greater than 98% conversion was observed by GC. The brown mixture was cooled with an ice bath to 3° C. and then the ice bath was removed to prevent freezing. To this was slowly added 17.5 mL of 0.5 N HCl and an ice bath was applied to maintain an internal temperature below 21° C. The mixture was then diluted with 10 mL MTBE and 5 mL of water before transfer to a separatory funnel and removal of the aqueous layer. The aqueous layer was extracted once with 15 mL MTBE and then the combined organic layers were washed with 20 mL water followed by 20 mL brine. The organic layer was then concentrated in vacuo to afford 1.27 g of rac-5 as a yellow oil (72 wt %). $^1$H NMR (400 MHz, CDCl$_3$) δ 3.24 (dt, 1H, J=2.6, 5.3 Hz), 2.25 (dt, 2H, J=2.6, 7.6 Hz), 1.96 (t, 1H, J=2.6 Hz), 1.92 (s, 1H, OH), 1.64 (pent, 2H, J=7.3 Hz), 1.38 (sext, 1H, J=6.9 Hz), 1.24 (sext, 1H, J=6.9 Hz), 0.93 (m, 1H), 0.72 (m, 1H), 0.35 (q, 1H, J=6.0 Hz); $^{13}$C NMR (100 MHz, CDCl$_3$) δ 84.49, 68.37, 52.45, 30.50, 27.74, 20.17, 18.01, 14.25; GC: HP1 (30 m×0.32 mm; 0.25 µm), 25 psi, 200° C. front inlet. 5 min @ 50° C., ramp 25° C./min to 250° C. then hold for 4 min, t$_r$(4)=7.15 min, t$_r$(rac-5)=6.72 min.

Example 4

Preparation of Acetic Acid racemic trans-2-pent-4-ynyl-cyclopropyl ester (rac-Compound 6)

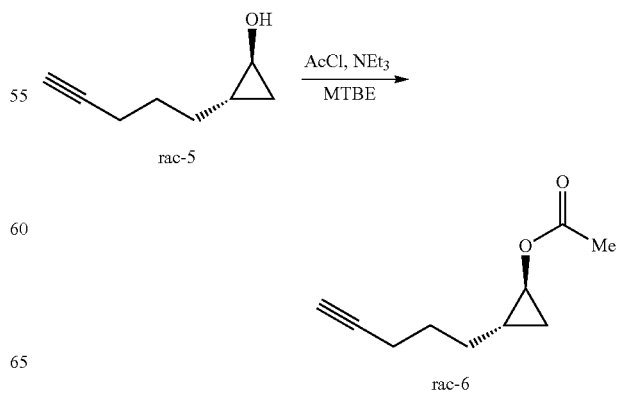

To a 5 L flask equipped with a nitrogen inlet, mechanical stirrer, dropping funnel and thermocouple under N₂ was added 31.2 g of rac-5 (251 mmol, 1.0 equiv), 350 mL of MTBE and 45.5 mL of triethylamine (327 mmol, 1.3 equiv) prior to cooling the solution in an acetone/ice bath to an internal temp of <5° C. To the solution was added from the dropping funnel 23.7 mL acetyl chloride (301 mmol, 1.1 equiv) over a 30 min period while maintaining the internal temp <10° C. The resulting slurry was then warmed to room temperature and aged for 2 hours. The reaction mixture was then diluted with 200 mL of water. The organic layer was washed with 200 mL of 2 N HCl and then with 300 mL of sat. NaHCO₃ prior to drying over MgSO₄. The solvent was removed in vacuo to give 41.8 g of rac-6. ¹H NMR (400 MHz, CDCl₃) δ 3.84 (dt, 1H, J=6.7, 2.9 Hz), 2.25 (dt, 2H, J=2.7, 7.0 Hz), 2.03 (s, 3H), 1.95 (t, 1H, J=2.6 Hz), 1.67 (m, 2H), 1.39 (m, 2H), 1.01 (m, 1H), 0.89 (m, 1H), 0.57 (q, 1H, J=6.5 Hz); ¹³C NMR (100 MHz, CDCl₃) δ 171.60, 84.15, 68.47, 54.20, 30.12, 27.40, 20.85, 17.92, 17.83, 11.81; GC: Restek RT-Bdex SA (30 m×0.25 mm×0.25 μm), 60 cm/s linear velocity, 20:1 split, 120° C. isothermal, t$_r$(5)=25.0, 29.6 min, t$_r$(6)=17.1, 17.5 min.

Example 5

Preparation of (1R,2R)-2-Pent-4-ynyl-cyclopropanol (ent-Compound 5)

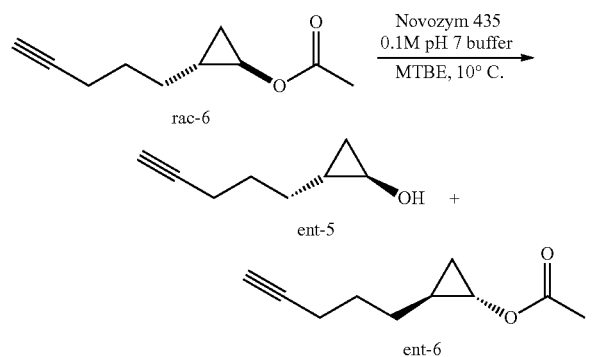

To a 1-L flask equipped with an overhead stirrer and temperature probe was added a 60 wt % solution of rac-6 in MTBE (44.8 g, 0.27 mol) and an additional 730 ml of MTBE that had been saturated with aqueous 0.1 M pH 7 phosphate buffer, giving a final solution concentration of rac-6 of 60 g/l. The flask was placed in an ice bath to maintain an internal temperature of approximately 10° C. throughout the hydrolysis reaction, which was initiated by the addition of 730 mg Novozym 435. The reaction was aged at 10° C. for approximately 4 hours until conversion had reached 41%, at which point the ee of ent-5 was 96%. The reaction mixture was then filtered through a 150-ml medium-pore glass filter funnel and the solid immobilized enzyme was washed three times with 80 ml MTBE. The resulting MTBE solution was then solvent switched to heptane. The mixture in heptane (39.2 kg, approximately 50 L) was applied to a Biotage Flash 400 L cartridge (40×60 cm, 40 kg silica gel, 60 angstrom, 40-63 um) and eluted sequentially with 165 L of 2.5:97.5, 75 L of 10:90, and 330 L of 25:75 EtOAc/heptane (v/v). After the mixture was applied to the column, 18 L fractions were taken. The rich cut fractions of the alcohol ent-5 were located by TLC (silica, 20% EtOAc/heptane) and then analyzed by GC (HP-1, 30 m×320 um×0.25 um film, 9.14 psi constant He pressure, 15:1 split, 50° C. for 5 min then 25 deg/min to 275° C. and hold 5 min, RT of alcohol 8.8 min). Fractions 15-21 were concentrated to give 3.48 kg (80 wt %, 92% ee) of the desired ent-5 (Compound 7).

GC: Restek RT-Bdex SA (30 m×0.25 mm×0.25 μm), 60 cm/s linear velocity, 20:1 split, 120° C. isothermal, t$_r$(5)=25.0, 29.6 min, t$_r$(6)=17.1, 17.5 min.

Example 6

Preparation of (S)-3,3-Dimethyl-2-((1R,2R)-2-pent-4-ynyl-cyclopropoxycarbonylamino)-butyric acid (Compound 8)

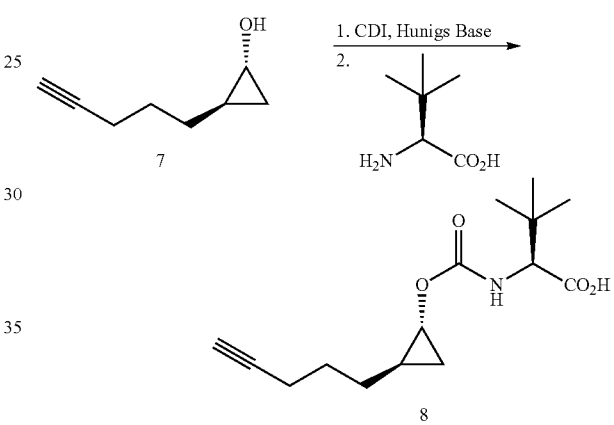

To a 50 L round bottom flask equipped with a mechanical stirrer, thermocouple and reflux condenser was added Compound 7 (3.477 kg @ 81 wt % by NMR, 92% ee) and 14.1 L (5 L/kg) of Hunigs base. To the resulting homogeneous solution was added CDI portion wise as a solid while maintaining the internal temperature between 21-25° C. The resulting slurry was aged at room temperature for 1 hour. To the slurry was added L-tert-leucine as a solid and the reaction mixture was heated to an internal temperature of 95° C. for 2.5 hours. The reaction mixture was cooled to room temperature and diluted with 17 L of water. The mixture was aged for 30 min to dissolve all the solids and then transferred to a 100 L cylindrical extractor. The aqueous layer was then washed with 12 L of MTBE. The aqueous layer was washed with 8 L of MTBE. The resulting aqueous layer was pH adjusted with concentrated HCl to a final pH of 1.5-2.0. The biphasic mixture was extracted with MTBE (2×12 L) and the combined organic phase was washed with 6 L of water followed by 5 L of brine.

The MTBE layer was then transferred via vacuum into a 50 L round bottom flask equipped with a mechanical stirrer, thermocouple, and batch concentrator and the solvent was removed under reduced pressure keeping the internal temperature of the batch <20° C. during the distillation. The solvent was then switched to cyclopentyl methyl ether (CPME) by flushing with ~5 L of CPME and then diluted to a final volume of ~20 L. This material was used in the next reaction without further purification.

An analytical sample was obtained by silica gel chromatography as a colorless oil: $^1$H NMR (CDCl$_3$, 400 MHz) δ 0.54 (q, 1H, J=6.4 Hz), 0.83 (m, 1H), 0.99 (m, 1H), 1.01 (s, 9H), 1.40 (m, 2H), 1.67 (m, 2H), 1.94 (t, 1H, J=2.6 Hz), 2.23 (m, 2H), 3.77 (br m, 1H), 4.20 (br m, 1H), 5.28 (br m, 1H), 9.40 (br s, 1H); $^{13}$C NMR (CDCl$_3$, 100 MHz) δ 11.8, 18.0, 26.5, 27.4, 30.1, 34.6, 55.0, 62.0, 68.4, 84.2, 156.7, 175.8.

Example 7

Preparation of 6-Methoxy-quinoxaline-2,3-diol (Compound 10)

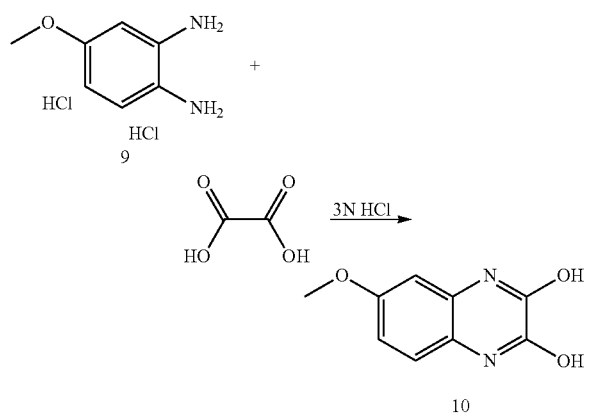

In a 50 L flask equipped with a mechanical stirrer, thermocouple and condenser was added 4-methoxy-1,2-phenylenediamine dihydrochloride salt (Compound 9) (2.65 kg @ 98 wt %, 12.30 mol), oxalic acid (1.582 kg @ 98 wt. %, 17.22 mol) and 3 N HCl$_{(aq)}$ (17.8 L) under nitrogen. The grey heterogeneous slurry was heated to 90° C. with steam for 7.25 hours. The reaction was monitored by HPLC. The resulting grey slurry was then cooled to an internal temperature of 20° C. overnight. The slurry was filtered, water (1.0-1.5 L/Kg) was used to help with the transfer. The light grey solids were washed with 2 cake volumes water (5.0-5.5 L/Kg). The solids were dried under vacuum/N$_2$ sweep for 24 hours, at which time the solids were still very wet. The product was then slurry washed with methanol, and dried over 48 hours at 40-45° C. in a vacuum oven to give Compound 10 as an off-white product of 99.95% purity by HPLC assay. There was no methanol by NMR and the KF=0.05 wt. % water.

HPLC Conditions: Zorbax Eclipse Plus C18 50×4.6 mm, 1.8 um, 1.5 mL/min, 210 nm, 25° C., Eluents: Water 0.1% H$_3$PO$_4$ (A), Acetonitrile (B). 90% A 0 min, 5% A 5 min, 5% A 6 min

| | |
|---|---|
| Compound 9 (diamine HCl salt) | 0.394 min |
| Compound 10 | 1.55 min (sometimes two peaks) |

Example 8

Preparation of 2,3-Dichloro-6-methoxyquinoxaline (Compound 11)

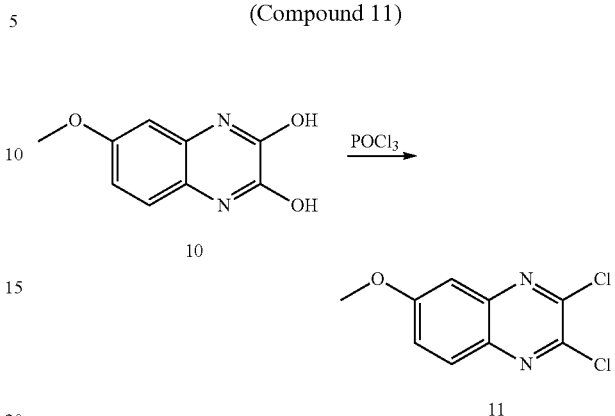

In a 22 L round bottomed flask equipped with a mechanical stirrer, thermocouple and condenser was added to 2,3-dichloro-6-methoxyquinoxalone Compound 10 (3.8 kg). Charged slowly at room temperature was POCl$_3$ (5.92 L @ 99%). The grey slurry was heated to 98° C. for 20 hours. After 2-3 hours the slurry turned from grey to green, then to yellow and finally turned homogeneous red. As the slurry became homogenous in POCl$_3$, significant amounts of HCl off-gassing were produced. The dark red, homogenous solution was allowed to cool slowly to below 80° C. At this point, 0.19 L of acetonitrile (5.0 L/Kg) was charged which produced a dark brown slurry. The reaction was cooled to 10-15° C. in an ice bath and reverse quenched into 45.6 L of cold water (12.0 L/Kg) in a 100 L cylindrical vessel. This exothermic quench was kept below 27° C. MeCN (~4 L) was used to aide in slurry transfer. The brown slurry was filtered and 5 L of water was used to wash the flask. The solids were washed with 1 cake volume of water (~5 L). The pH of the filtrate was acidic. The solids were next displacement washed with 2 cake volumes of 5% sodium bicarbonate (~20.00 L). The pH was between 8-9. A slurry wash was performed with 2 cake volumes of water (20 L total). The pH did not change. The solids were dried for 72 hours under reduced pressure and nitrogen flow to give tan product Compound 11 of 99.5% purity by HPLC assay with KF=0.5 wt. % water.

HPLC Conditions: Zorbax Eclipse Plus C18 50×4.6 mm, 1.8 um, 1.5 mL/min, 210 nm, 25° C.; Eluents: Water 0.1% H$_3$PO$_4$ (A), Acetonitrile (B). 90% A 0 min, 5% A 5 min, 5% A 6 min.

| | |
|---|---|
| Compound 10 | 1.55 min (sometimes two peaks) |
| Compound 11 | 4.55 min |

An analytical sample was obtained by silica gel chromatography and as a colorless foam: $^1$H NMR (CDCl$_3$, 400 MHz) δ 0.50 (q, 1H, J=6.3 Hz), 1.04 (br s, 11 H), 1.20 (br s, 3H), 1.45 (br s, 13 H), 1.72 (m, 2H), 2.40 (m, 1H), 2.63 (m, 1H), 2.93 9m, 2H), 3.68-3.94 (m, 9H), 4.15 (br m, 1H), 4.46 and 4.60 (t, due to rotamers, 1H, J=7.8 Hz), 5.27 (br m, 1H), 5.78 (br m, 1H), 7.18 (m, 1H), 7.20 (m, 1H), 7.85 (m, 1H); $^{13}$C NMR (CDCl$_3$, 100 MHz) δ 11.9, 18.5, 26.6, 27.0, 28.1, 28.3, 28.4, 29.1, 30.9, 32.9, 34.1, 35.7, 36.6, 49.4, 52.1, 52.2, 52.4, 55.1, 55.7, 57.7, 58.2, 62.3, 73.5, 74.1, 80.7, 106.0, 118.8, 128.5, 133.7, 141.1, 148.2, 153.9, 154.5, 155.3, 157.1, 160.4, 173.2, 173.3, 174.4.

Example 9

Preparation of (2S,4R)-4-(3-chloro-7-methoxyquinoxalin-2-yloxy)-2-(methoxycarbonyl)pyrrolidinium methanesulfonate (14)

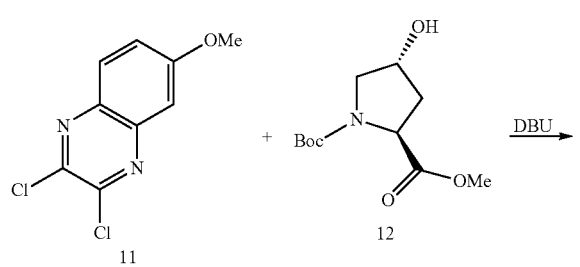

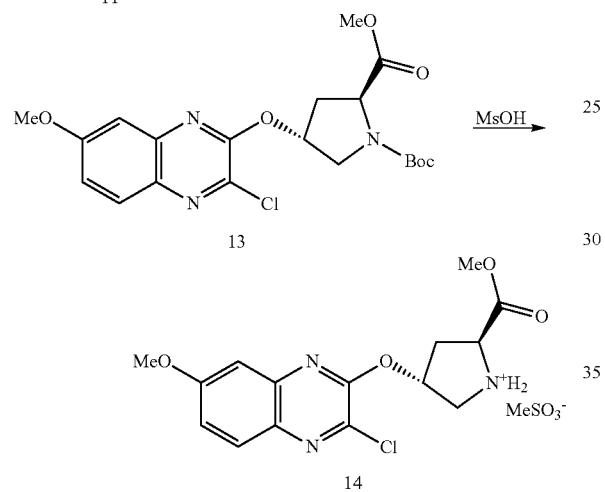

To a slurry of 2,3-dichloroquinoxaline 11 (100 g, 0.437 mol) and N-Boc-4-trans-hydroxy-L-proline methyl ester (12, 118 g, 0.48 mol) in DMAc (500 ml, KF <150) at ambient temperature was added DBU (86 g, 0.568 mol). The slurry was agitated at 40-45° C. for ~35 hours. The batch was then cooled to 15° C. Ethyl acetate (1.2 L) followed by citric acid (10%, 504 mL, 162 mmol) was added while the internal temperature was maintained <25° C. The organic phase was washed with a solution of 10% citric acid (200 mL) and water (200 mL) followed by water (400 mL×2). The organic phase was azeotropically dried and solvent switched to MeCN at a final volume of ~880 mL. MeSO₃H (36 mL, 0.555 mol) was added and the reaction mixture was aged at 40° C. for ~16 hours. To the reaction slurry was added MTBE (1.05 L) dropwise over 2 hours at 35° C. Then, the batch was further cooled to 0-5° C. and aged for 2-3 hours before filtration. The wet cake was displacement washed with 30% MeCN in MTBE (600 mL×2), and vacuum oven dried at 40° C. to give the product 14.

$^1$H NMR (400 MHz, d$_6$-DMSO) δ 9.74 (s, br, 2 H), 7.86 (d, J=9.2 Hz, 1 H), 7.34 (dd, J=9.2, 2.8 Hz, 1 H), 7.26 (d, J=2.8 Hz, 1 H), 5.77 (m 1 H), 4.69 (dd, J=10.6, 7.6 Hz, 1 H), 3.92 (s, 3 H), 3.89 (dd, J=13.2, 5.2 Hz, 1 H), 3.81 (s, 3 H), 3.63 (m, 1 H), 2.71 (m, 1 H), 2.60 (m, 1 H), 2.35 (s, 3 H).

$^{13}$C NMR (100 MHz, d$_6$-DMSO) δ 168.3, 161.0, 151.8, 140.4, 135.4, 133.3, 128.6, 119.8, 106.0, 75.6, 58.0, 56.0, 53.2, 50.5, 39.6, 33.9.

HPLC conditions: Hypersil Gold PFP column, 150×4.6 mm, 3.0 um; Column temperature of 40° C.; Flow rate of 1.8 mL/min; and Wavelength of 215 nm.

| Gradient: | | |
|---|---|---|
| min | CH₃CN | 0.1% H₃PO₄ |
| 0 | 25 | 75 |
| 12 | 70 | 30 |
| 12.1 | 25 | 75 |
| 14 | 25 | 75 |

| Retention times: | min. |
|---|---|
| Dichloroquinoxaline 11 | 7.8 |
| Proline quinoxaline 13 | 9.8 |
| De-Boc quinoxaline 14 | 3.6 |

Example 10

Preparation of (S)-2-(((1R,2R)-2-(5-(6-methoxy-3-((3R,5S)-5-(methoxycarbonyl)pyrrolidin-3-yloxy)quinoxalin-2-yl)pent-4-ynyl)cyclopropoxy)carbonylamino)-3,3-dimethylbutanoic acid 16 and alkyne macrocyclic ester (17)

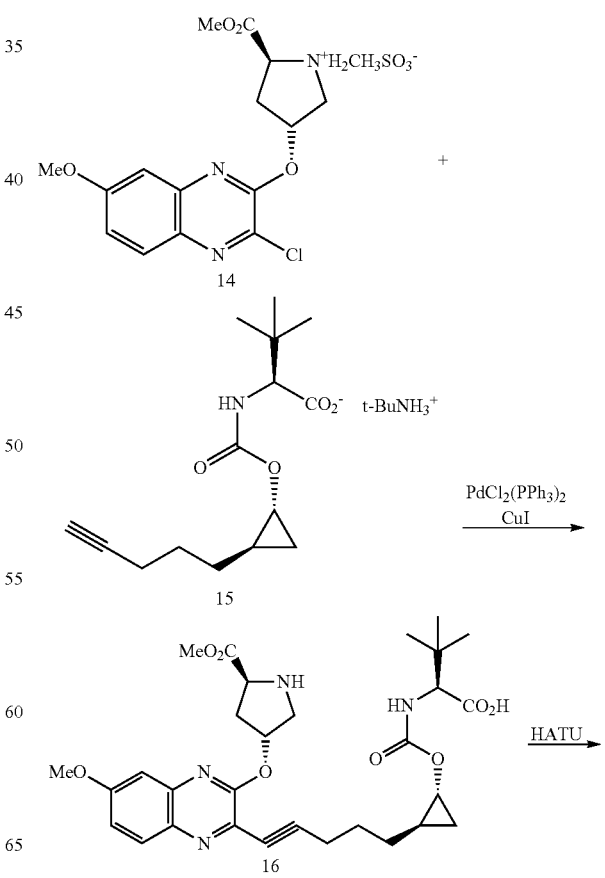

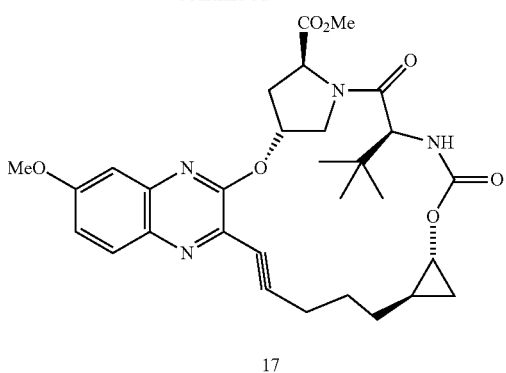

17

To a three-neck flask were added copper(I) iodide (0.219 g, 1.152 mmol), chloroquinoxaline MsOH salt 14 (50 g, 115 mmol), alkyne acid TBA salt 15 (49.3 g, 121 mmol), and bis(triphenylphosphine)palladium(II) dichloride (0.404 g, 0.573 mmol). The flask was vacuumed degassed with $N_2$. MeOH (500 ml) was added and the reaction mixture was vacuum degassed again with $N_2$. Triethylamine (32.1 ml, 230 mmol) was added. The reaction solution was aged at 35° C. for 3-5 hours. The batch was then concentrated to a volume of ~100 mL in vacuum. THF (250 mL) and EtOAc (250 mL) were added. The reaction mixture was cooled to below 5° C. HCl solution (1 N, ~180 mL) was added slowly at below 5° C. until the reaction solution was pH adjusted to ~2. NaCl aq. solution (10%, 350 mL) was added. The separated aqueous phase was back-extracted with a solution of THF (250 mL) and EtOAc (250 mL). The combined organic phase was washed with 10% NaCl aq. solution (500 mL). The organic phase was azeotropically concentrated in vacuum with THF at below 20° C. until the KF of the solution was less than 500 ppm. Then, the reaction solvent was switched to DMAc (650 mL) in vacuum at below 20° C.

A solution of HATU (55.1 g, 145 mmol) in DMAc (650 mL) at ambient temperature was vacuumed degassed with $N_2$. The solution was then cooled to 0° C. and DIPEA (58.5 mL, 335 mmol) was added dropwise at below 0-5° C. Then, the above solution of alkyne quinoxaline acid 16 (65 g assay, 112 mmol) in DMAc was added dropwsie over 10 hours, while maintaining the internal temperature at 0° C. After addition, the batch was agitated at 0° C. for additional 2 hours. EtOAc (750 mL) was added at below 5° C. A solution of 10% NaCl aq. solution (400 mL), water (125 mL) and 1 N HCl solution (100 mL) was slowly added while maintaining the batch temperature at below 5° C. The solution was then adjusted to pH=2 with 1 N HCl (~25 mL). The separated aqueous phase was back-extracted with EtOAc (500 mL). The combined organic phase was washed with 10% NaCl aq. solution (500 mL). After 10% NaCl aq. solution (500 mL) was added to the combined organic phase, the mixed solution was cooled to 0-5° C. 1 N NaOH aq. solution (~25 mL) was added to adjust the pH=~7. The separated organic phase was filtered through Celite and solvent switched to IPA at a final volume of 300 mL. Acetic acid (5.0 mL) was added, and the batch was then heated up to reflux for 30 min. The slurry was cooled to 60° C. and water (250 mL) was added dropwise over 1 hour. After addition, the batch was aged for additional 30 min before slowly cooling to ambient temperature in about 2 hours. After aging at least 1 hour, the batch was filtered. The wet cake was displacement washed with 50% aq IPA (100 mL). Suction dry at ambient temperature afforded 56 g of macrocyclic alkyne ester 17.

$^1$H NMR (400 MHz, CDCl$_3$) δ 7.80 (d, J=9.2 Hz, 1 H), 7.17 (dd, J=9.2, 2.8 Hz, 1 H), 7.04 (d, J=2.8 Hz, 1 H), 5.82 (t, J=4.2 Hz, 1 H), 5.26 (d, J=9.9 Hz, 1 H), 4.62 (dd, J=10.3, 7.3 Hz, 1 H), 4.51 (d, J=11.6 Hz, 1 H), 4.40 (d, J=9.9 Hz, 1 H), 4.03 (dd, J=11.6, 4.4 Hz, 1 H), 3.91 (s, 3 H), 3.87 (m, 1 H), 3.73 (s, 3 H), 2.85 (dt, J=12.1, 4.2 Hz, 1 H), 2.76 (d, J=14.4, 7.3 Hz, 1 H), 2.49 (dt, J=12.2, 5.4 Hz, 1 H), 2.30 (ddd, J=14.6, 10.1, 4.2 Hz, 1 H), 1.99 (m, 1 H), 1.82 (m, 1 H), 1.74 (m, 1 H), 1.08 (s, 9 H), 0.92 (m, 2 H), 0.76 (m, 1 H), 0.47 (m, 1 H).

$^{13}$C NMR (100 MHz, CDCl$_3$) δ 172.3, 171.3, 161.2, 157.4, 156.3, 140.4, 134.3, 130.2, 129.5, 119.5, 105.7, 98.9, 75.5, 75.2, 59.4, 58.1, 55.7, 55.6, 54.1, 52.3, 35.3, 35.0, 29.9, 28.0, 26.3, 18.7, 18.3, 10.3.

IPC HPLC conditions: Ascentis Express C18 column, 100×4.6 mm, 2.7 micron; Column temperature of 40° C.; Flow rate of 1.8 mL/min; and Wavelength of 215 nm.

| Gradient: | | |
|---|---|---|
| min | CH$_3$CN | 0.1% H$_3$PO$_4$ |
| 0 | 10 | 90 |
| 6 | 95 | 5 |
| 9 | 95 | 5 |
| 9.1 | 10 | 90 |

| Retention times: | min. |
|---|---|
| De-Boc quinoxaline 14 | 2.3 |
| Alkyne quinoxaline acid 16 | 3.3 |
| Alkyne macrocyclic ester 17 | 5.7 |

Example 11

Preparation of Macrocyclic Ester 18

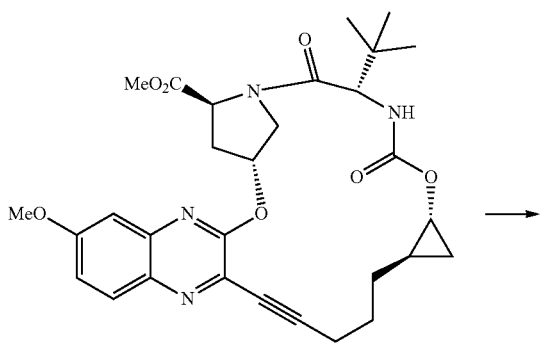

17

Example 12

Preparation of Macrocyclic Acid (19)

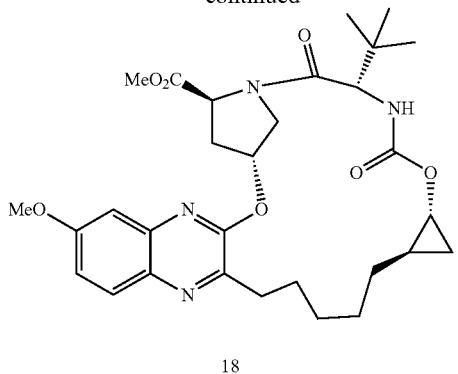

18

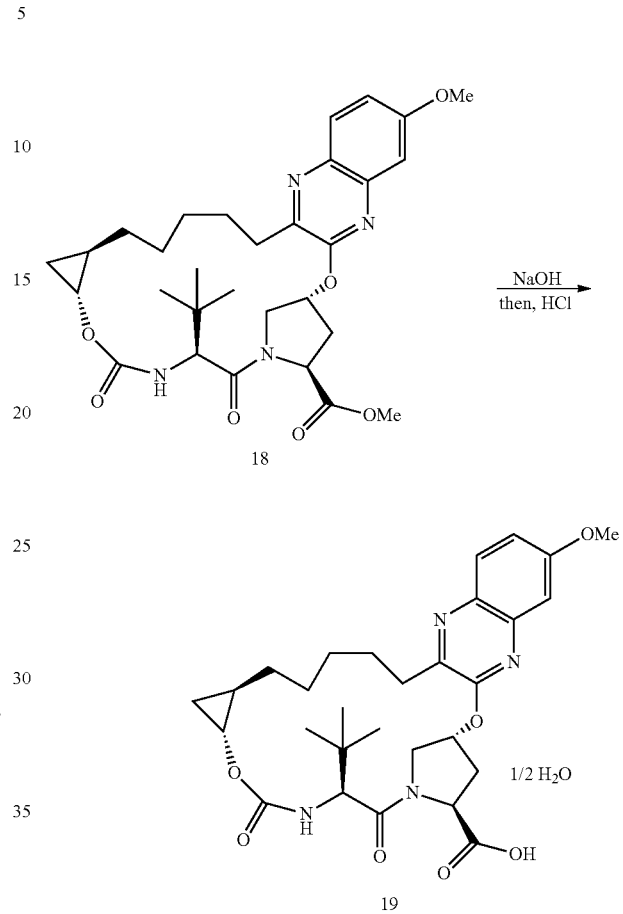

A mixture of alkyne macrocyclic ester 17 (10.0 g, 17.71 mmol) and 5% Pd/C 50% wet (3.5 g, 0.822 mmol) in THF (100 mL) was hydrogenated at ambient temperature under 40 psig of hydrogen for at least 10 hours. Upon reaction completion, the batch was filtered through Celite and the filtered catalyst was washed with THF (100 mL). The combined filtrate was solvent switched to IPA in vacuum at a final volume of ~50 mL. The slurry was heated up to reflux for about 1 hour. The batch was then cooled to 50° C. and water (30 mL) was added dropwise over 1 hour. The batch was slowly cooled to below 0° C. over 2 hour and stirred at 0° C. for additional 1 hour before filtration. The wet cake was washed with a cold solution (0-5° C.) of 57% IPA in water (17.5 mL). Suction dry at ambient temperature gave 8.5 g of the desired macrocyclic ester 18.

$^1$H NMR (400 MHz, CDCl$_3$) δ 7.83 (d, J=9.2 Hz, 1 H), 7.18 (dd, J=9.2, 2.8 Hz, 1 H), 7.1 (d, J=2.8 Hz, 1 H), 5.98 (t, J=4.0 Hz, 1 H), 5.24 (d, J=9.9 Hz, 1 H), 4.60 (dd, J=10.7, 7.3 Hz, 1 H), 4.46 (d, J=11.9 Hz, 1 H), 4.40 (d, J=10.0 Hz, 1 H), 4.01 (dd, J=11.6, 4.0 Hz, 1 H), 3.93 (s, 3 H), 3.80 (m, 1 H), 3.75 (s, 3 H), 2.90 (ddd, J=13.7, 11.5, 4.8 Hz, 1 H), 2.79 (ddd, J=13.7, 12.1, 4.8 Hz, 1 H), 2.69 (dd, J=14.2, 6.5 Hz, 1 H), 2.28 (ddd, J=14.5, 10.7, 4.3 Hz, 1 H), 1.76 (m, 2 H), 1.66 (m, 2 H), 1.52 (m, 3 H), 1.09 (s, 9 H), 0.99 (m, 1 H), 0.92 (m, 1 H), 0.67 (m, 1 H), 0.46 (m, 1 H).

$^{13}$C NMR (100 MHz, CDCl$_3$) δ 172.4, 171.5, 160.4, 157.5, 155.1, 148.7, 140.1, 134.6, 129.4, 118.7, 106.1, 74.4, 59.4, 58.2, 55.8, 55.5, 54.4, 52.5, 35.7, 35.2, 34.0, 30.9, 29.5, 28.6, 28.3, 26.5, 18.9, 11.2.

IPC HPLC conditions: Ascentis Express C18 Column, 100×4.6 mm, 2.7 micron; Column temperature or 40° C.; Flow rate or 1.8 mL/min; and Wavelength of 215 nm.

| Gradient: | | |
|---|---|---|
| min | CH$_3$CN | 0.1% H$_3$PO$_4$ |
| 0 | 10 | 90 |
| 6 | 95 | 5 |
| 9 | 95 | 5 |
| 9.1 | 10 | 90 |

| Retention times: | min. |
|---|---|
| Alkyne macrocyclic ester 17 | 5.7 |
| cis-Alkene macrocyclic_ester (reaction intermediate) | 6.0 |
| trans-Alkene macrocyclic_ester (reaction intermediate) | 6.1 |
| Compound 18 | 6.2 |

To a slurry of macrocyclic ester 18 (90 g, 158.3 mmol) in MeOH (720 mL) at ambient temperature was added 2 M NaOH (237.4 mL, 475 mmol) dropwise. The reaction mixture was aged at 50° C. for 2-3 hours. The reaction solution was cooled to 35-40° C. and 5 N HCl in 50% aq MeOH (70 mL) was added dropwise. The batch was seeded with free acid hemihydrate 19 (~100 mg) and aged for 30 min to 1 hour at 40° C. Additional 5 N HCl in 50% aq MeOH (30 mL) was added dropwise over 2-4 hours at 40° C. The slurry was aged additional 1 hour before cooling to ambient temperature. The slurry was aged for additional 1 hour before filtration. The wet cake was washed with 65% MeOH in water (3×270 mL, displacement wash, slurry wash and displacement wash). Suction dry at ambient temperature or vacuum oven dry with dry N$_2$ sweep at 60-80° C. gave 85.6 g of macrocyclic acid hemihydrate 19 as an off-white solid.

$^1$H NMR (400 MHz, CDCl$_3$) δ 7.85 (d, J=9.0 Hz, 1 H), 7.19 (dd, J=9.0, 2.8 Hz, 1 H), 7.13 (d, J=2.8 Hz, 1 H), 5.99 (t, J=3.9 Hz, 1 H), 5.45 (d, J=9.9 Hz, 1 H), 4.80 (s, br, 2 H, COOH, hemihydrate H$_2$O), 4.64 (dd, J=10.4, 7.4 Hz, 1 H), 4.49 (d, J=11.6 Hz, 1 H), 4.44 (d, J=10.0 Hz, 1 H), 3.99 (dd, J=11.7, 4.0 Hz, 1 H), 3.94 (s, 3 H), 3.81 (m, 1 H), 2.90 (ddd, J=13.8, 11.8, 4.8, 1 H), 2.80 (ddd, J=13.8, 11.8, 4.8 Hz, 1 H), 2.71 (dd, J=14.3, 7.3, 1 H), 2.42 (ddd, J=14.4, 10.6, 4.2 Hz, 1 H), 1.76 (m, 2 H), 1.66 (m, 2 H), 1.52 (m, 3 H), 1.07 (s, 9 H), 0.96 (m, 2 H), 0.67 (m, 1 H), 0.47 (m, 1 H).

$^{13}$C NMR (100 MHz, CDCl$_3$) δ 174.5, 172.1, 160.5, 157.6, 155.1, 148.6, 141.0, 134.3, 129.1, 118.9, 106.1, 74.3, 59.6, 58.3, 55.6, 54.6, 35.6, 35.3, 33.7, 30.8, 29.4, 28.6, 28.3, 26.5, 18.9, 11.2.

IPC HPLC conditions: Hypersil Gold PFP Column, 150× 4.6 mm, 3.0 µm, Column temperature of 40° C.; Flow rate of 1.8 mL/min; and Wavelength of 215 nm

| Gradient: | | |
|---|---|---|
| min | CH$_3$CN | 0.1% H$_3$PO$_4$ |
| 0 | 25 | 75 |
| 12 | 80 | 20 |
| 12.1 | 25 | 75 |
| 14 | 25 | 75 |
| Retention times: | min. | |
| Compound 18 | 6.78 | |
| Compound 19 | 5.41 | |

Example 13

Preparation of Compound A

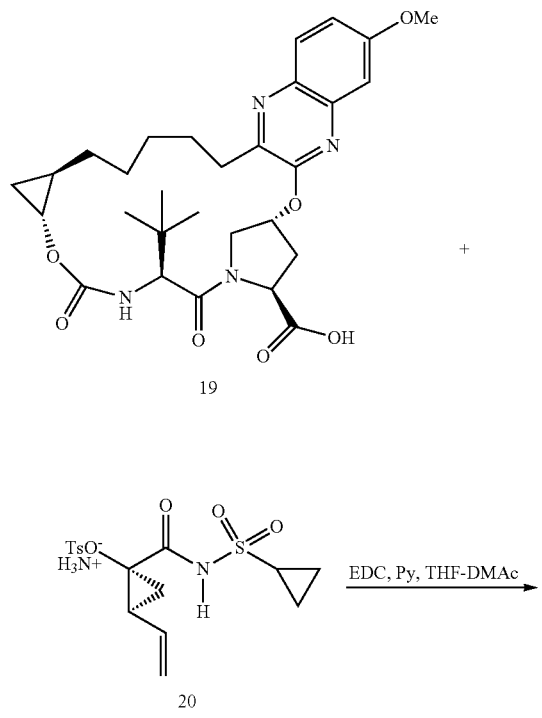

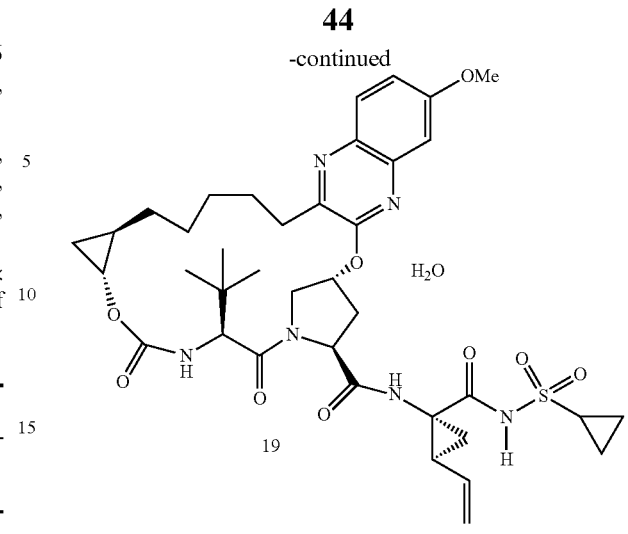

Compound A hydrate

Macrocyclic acid hemihydrate 19 (10.16 g, 18.03 mmol) was dissolved in THF (50-90 mL). The solution was azetropically dried at a final volume of 100 mL. Sulfonamide pTSA salt 20 (7.98 g, 1.983 mmol) followed by DMAc (15 mL) was added at ambient temperature. The batch was cooled to 0-10° C. and pyridine (10 mL) was added dropwise. Then, EDC HCl (4.49 g, 23.44 mmol) was added in portions or one portion at 0-10° C. The reaction mixture was aged at 0-10° C. for 1 hour, then warmed to 15-20° C. for 2-4 hours. MeOAc (100 mL) followed by 15 wt % citirc acid in 5% NaCl in water (50 mL) was added, while the internal temperature was maintained to <25° C. with external cooling. The separated organic phase was washed with 15 wt % citirc acid in 5% NaCl in water (50 mL) followed by 5% NaCl (50 mL). The organic phase was solvent switched to acetone at a final volume of ~80 mL. Water (10 mL) was added dropwise at 35-40° C. The batch was seeded with Compound A monohydrate form III (~10 mg) and aged for 0.5-1 hour at 35-40° C. Additional water (22 mL) was added dropwise over 2-4 hours at 35-40 C. The slurry was aged at 20° C. for 2-4 hours before filtration. The wet cake was displacement washed with 60% acetone in water (40 mL×2). Suction dry at ambient temperature gave Compound A monohydrate form III as a white solid.

$^1$H NMR (400 MHz, CDCl$_3$) δ 9.95 (s, br, 1 H), 7.81 (d, J=9.1 Hz, 1 H), 7.18 (dd, J=9.1, 2.7 Hz, 1 H), 7.16 (s, br, 1 H), 7.13 (d, J=2.7 Hz, 1 H), 5.96 (t, J=3.8 Hz, 1 H), 5.72 (m, 1 H), 5.68 (d, J=10.1 Hz, 1 H), 5.19 (d, J=17.1 Hz, 1 H), 5.07 (d, J=10.1 Hz, 1 H), 4.52 (d, J=11.4 Hz, 1 H), 4.45 (d, J=9.8 Hz, 1 H), 4.36 (d, J=10.5, 6.9 Hz, 1 H), 4.05 (dd, J=11.5, 3.9 Hz, 1 H), 3.93 (s, 3 H), 3.78 (m, 1 H), 2.90 (m, 1 H), 2.82 (tt, J=8.0, 4.8 Hz, 1 H), 2.74 (dt, J=13.2, 4.8 Hz, 1 H), 2.59 (dd, J=14.0, 6.7 Hz, 1 H), 2.40 (ddd, J=14.0, 10.6, 4.0 Hz, 1 H), 2.10 (dd, J=17.7, 8.7 Hz, 1 H), 1.98 (2 H, mono hydrate H$_2$O), 1.88 (dd, J 8.2, 5.9 Hz, 1 H0, 1.74 (m, 3 H), 1.61 (m, 1 H), 1.50 (m, 3 H), 1.42 (dd, J=9.6, 5.8 Hz, 1 H), 1.22 (m, 2 H), 1.07 (s, 9 H), 0.95 (m, 4 H), 0.69 (m, 1 H), 0.47 (m, 1 H).

$^{13}$C NMR (100 MHz, CDCl$_3$) δ 173.5, 172.1, 169.1, 160.4, 157.7, 154.9, 148.4, 141.0, 134.3, 132.7, 129.1, 118.8, 118.7, 106.5, 74.4, 59.6, 59.4, 55.8, 55.5, 54.9, 41.8, 35.4, 35.3, 35.2, 34.3, 31.2, 30.7, 29.5, 28.6, 28.2, 26.6, 22.6, 18.7, 11.2, 6.31, 6.17.

HPLC conditions: Ascentis Express Column, 10 cm×4.6 mm×2.7 µm; Column temperature of 40° C.; Flow rate of 1.8 mL/min; and Wavelength of 215 nm

| Gradient: | | |
|---|---|---|
| min | CH₃CN | 0.1% H₃PO₄ |
| 0 | 20 | 80 |
| 5 | 55 | 45 |
| 15 | 55 | 45 |
| 25 | 95 | 5 |
| 27 | 95 | 5 |
| 27.1 | 20 | 80 |
| 32 | 20 | 80 |
| Retention times: | | min. |
| Compound A | | 14.50 |

Example 14

Alternative Procedure for Making Compound A

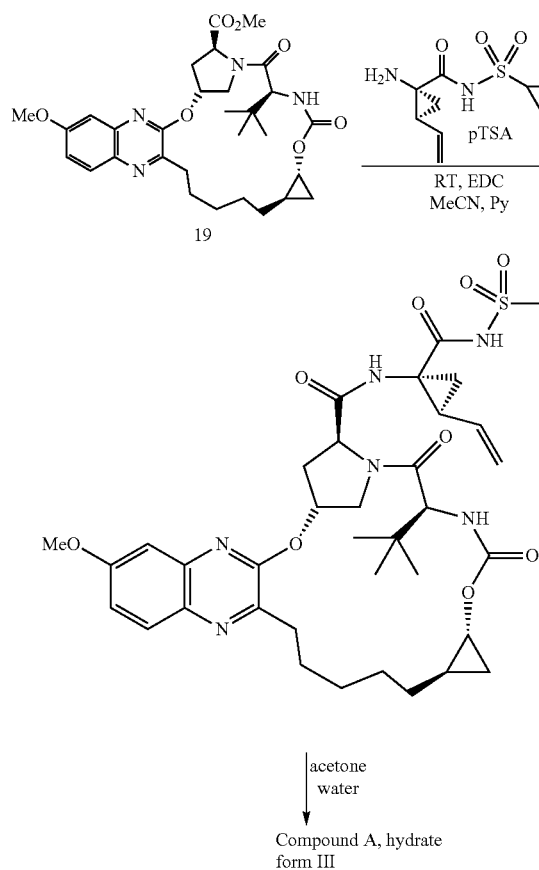

To a 50 L flask equipped with overhead stirring was added macrocyclic acid 19 (1.06 kg crude, 1.00 eq), amine-pTSA (862 g crude, 1.12 q) and MeCN 7.42 L at 19° C. The slurry was cooled in a water bath, pyridine (2.12 L, 13.8 eq) was added, aged 15 minutes, and then added EDC (586 g, 1.60 eq) in one portion, aged 1.5 hours while it turned into a clear homogeneous solution.

The solution cooled in a water bath, then quenched with 2 N HCl (1.7 L), seeded (9.2 g), aged 15 minutes, and the rest of the aqueous HCl was added over 2.5 hours. A yellow slurry was formed. The slurry was aged overnight at RT, filtered, washed with MeCN/water (1:1 v/v) 8 L, to obtain Compound A (Hydrate II).

Compound A was dissolved in acetone 4 L at RT, filtered and transferred to a 12 L RBF with overhead stirring, rinsed with extra acetone 1 L, heated to 50° C., water 0.9 L was added, seeded 10 g, aged 15 minutes, then added water 0.8 L over 2.5 hours, extra water 3.3 v over 2.5 hours was added, stopped heating, cooled to RT, aged at RT overnight, filtered, washed with water/acetone (1:1 v/v) 4 L, and dried in air under vacuum. Compound A Hydrate III, 670 g, was obtained as an off-white solid.

Example 15

Alternative Preparation of Macrocyclic Ester (18)

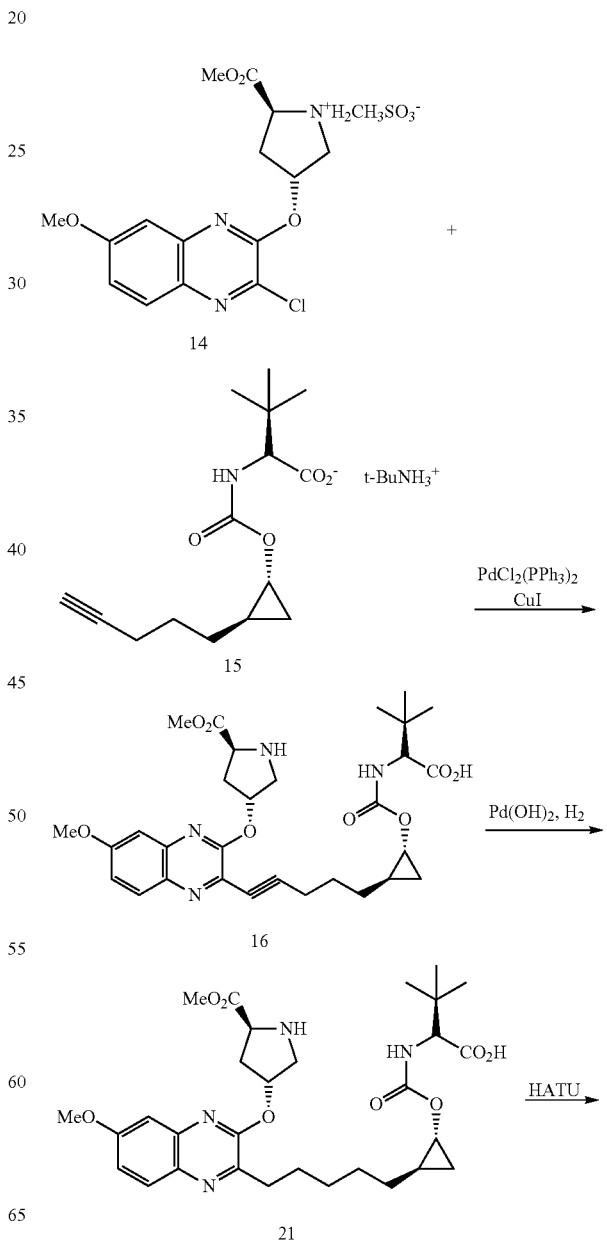

-continued

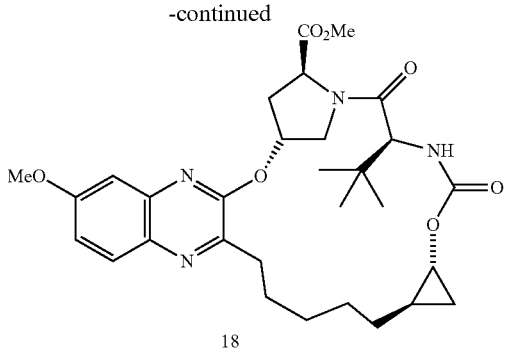

18

To a three-neck flask were added copper(I) iodide (0.020 g, 0.104 mmol), chloroquinoxaline MsOH salt 14 (4.5 g, 10.5 mmol), alkyne acid TBA salt 15 (4.4 g, 10.9 mmol), and bis(triphenylphosphine)palladium(II) dichloride (0.036 g, 0.052 mmol). The flask was vacuumed degassed with $N_2$. MeOH (45 ml) was added and the reaction mixture was vacuum degassed again with $N_2$. Triethylamine (2.89 ml, 20.7 mmol) was added. The reaction solution was aged at 35° C. for 3-5 hours. The batch was then concentrated to a volume of ~9 mL in vacuum. THF (23 mL) and EtOAc (23 mL) were added. The reaction mixture was cooled to below 5° C. HCl solution (1 N, ~16 mL) was added slowly at below 5° C. until the reaction solution was pH adjusted to ~2. NaCl aq. solution (10%, 32 mL) was added. The separated aqueous phase was back-extracted with a solution of THF (23 mL) and EtOAc (23 mL). The combined organic phase was washed with 10% NaCl aq. solution (45 mL). The solvent was switched to MeOH (75 mL) in vacuum at below 20° C.

To the reaction mixture was added DARCO KB-B (1.0 g), and the resulting suspension was stirred at 20° C. for 1 hour followed by filtration through Celite. The wet cake was washed with MeOH (25 mL). The combined filtrate was hydrogenated in the presence of Pearlman's catalyst (1.2 g, 20% $Pd(OH)_2$ on carbon, 50% wet) under 1 atmosphere of hydrogen at ambient temperature for at least 5 hours. Upon reaction completion, the suspension was filtered through Celite and the filtrate containing acid 21 was solvent switched to DMAc (65 mL).

A solution of HATU (5.05 g, 13.3 mmol) in DMAc (65 mL) at ambient temperature was vacuumed degassed with $N_2$. The solution was cooled to 0° C. and DIPEA (5.4 mL, 30.9 mmol) was added dropwise at 0-5° C. Then, the above solution of acid 21 (5.98 g assay, 10.2 mmol) in DMAc was added dropwsie over 10 hours, while maintaining the internal temperature at 0° C. After addition, the batch was agitated at 0° C. for additional 2 hours to afford macrocyclic ester 18. The workup procedure and isolation of macrocyclic ester 18 were the same as described in Example 11.

Example 16

Compound 19 Characterization

Compound 19 was characterized using different techniques, including X-ray diffraction and solid-state carbon-13 nuclear magnetic resonance (NMR) spectra. The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source.

The carbon-13 spectra were recorded using a Bruker 4 mm HXY triple resonance CPMAS, and a Bruker 4 mm H/FX double resonance CPMAS probe, respectively. The carbon-13 spectra were collected utilizing proton/carbon-13 variable-amplitude cross-polarization (VACP) with a contact time of 3 ms, and a pulse delay of 3 s, while magic-angle spinning (MAS) the samples at 13 kHz. A line broadening of 30 Hz was applied to the carbon-13 spectra before Fourier Transformation. Chemical shifts are reported on the TMS scale using the carbonyl carbon of glycine (176.7 ppm) as a secondary reference.

FIG. 1 provides a characteristic X-ray diffraction pattern of the crystalline Compound 19 hydrate I. The hydrate exhibited characteristic reflections corresponding to d-spacings of:

TABLE 7

| Pos. [°2Th.] | Height [cts] | d-spacing [Å] |
|---|---|---|
| 8.7 | 723.1 | 10.2 |
| 22.2 | 277.9 | 4.0 |
| 23.5 | 216.8 | 3.8 |
| 8.3 | 214.3 | 10.7 |
| 14.7 | 199.8 | 6.0 |
| 7.6 | 178.7 | 11.7 |
| 22.8 | 101.6 | 3.9 |
| 11.3 | 87.9 | 7.9 |

FIG. 2 shows the solid state carbon-13 CPMAS NMR spectrum for the Compound 19 hydrate 1. Characteristic peaks for hydrate I are observed at 174.7, 172.0, 161.4, 156.8, 156.3, 149.5, 142.1, 133.9, 128.2, 121.3, 105.0, 76.9, 60.7, 57.5, 55.1, 53.5, 35.8, 34.7, 33.4, 32.4, 29.5, 27.8, 24.0, and 20.2 ppm.

Example 18

Compound 14 Methylsulfonic acid, MeCN Solvate Characterization

The MeCN solvate of compound 18 methylsulfonic acid salt, was characterized by X-ray diffraction. The results are shown in FIG. 3. Characteristic peaks are provided in Table 8.

The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source.

TABLE 8

| d-spacing [Å] | Pos. [°2Th.] | Height [cts] | Rel. Int. [%] |
|---|---|---|---|
| 16.8 | 5.3 | 660.4 | 100.0 |
| 7.4 | 12.0 | 476.3 | 72.1 |
| 6.3 | 14.1 | 240.5 | 36.4 |
| 3.9 | 22.7 | 176.9 | 26.8 |
| 9.5 | 9.3 | 168.8 | 25.6 |
| 5.5 | 16.1 | 134.4 | 20.3 |
| 4.2 | 20.9 | 105.0 | 15.9 |
| 5.2 | 17.2 | 77.1 | 11.7 |
| 3.4 | 25.8 | 29.0 | 4.4 |
| 2.8 | 32.3 | 25.4 | 3.9 |

None of the references described throughout the present application are admitted to be prior art to the claimed invention.

What is claimed is:

1. A method of making Compound A or a salt thereof:

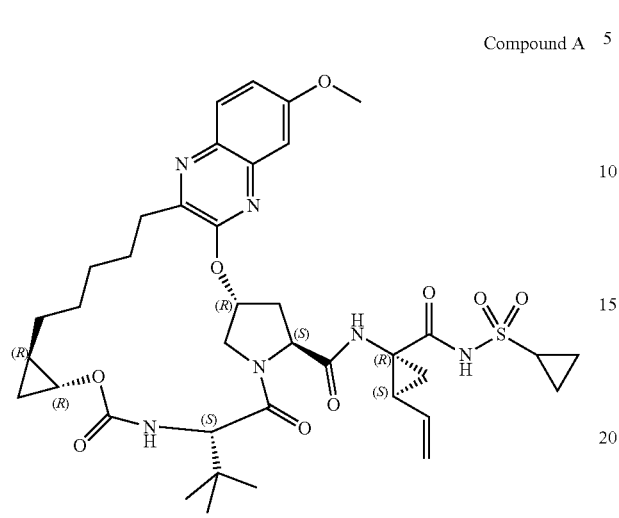

Compound A comprising the steps of:
(i) reacting

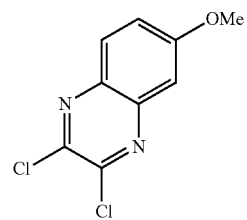

(Compound 11)

with

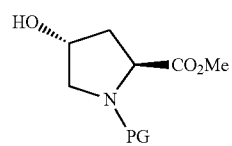

(Compound 12)

by SNAR replacement to form Compound 13 and deprotecting

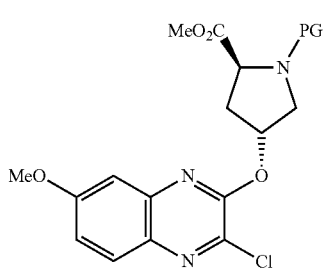

(Compound 13)

to form

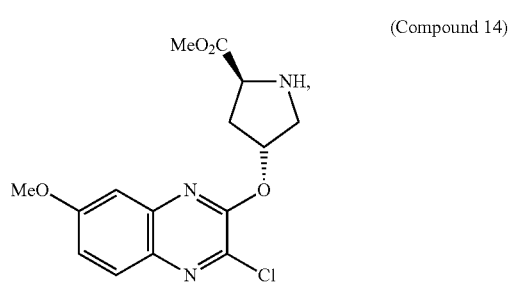

(Compound 14)

wherein Compound 13 is not isolated prior to deprotection, and PG is a protecting group;

(ii) coupling Compound 14 with

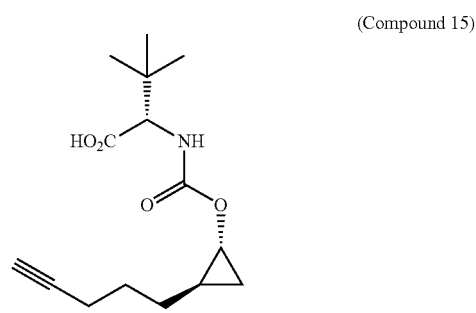 [SMILES: C#CCCC[C@@H]1C[C@H]1OC(=O)N[C@H](C(=O)O)C(C)(C)C]

(Compound 15)

to produce

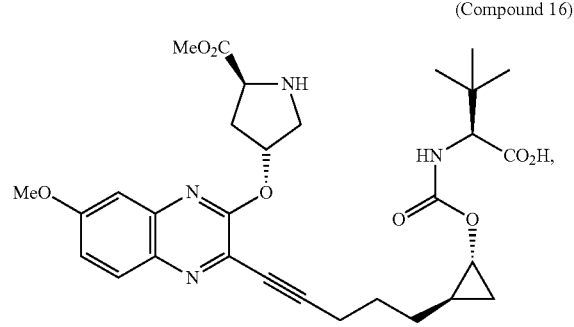

(Compound 16)

(iii) without isolating Compound 16, hydrogenating Compound 16 to produce

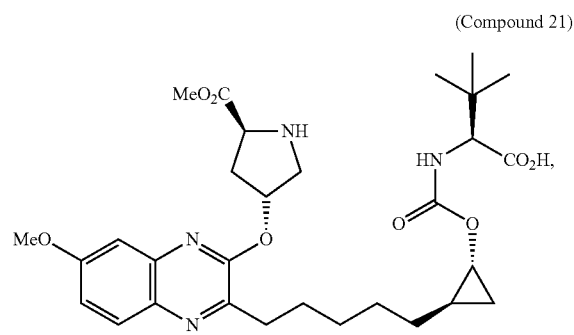

(Compound 21)

(iv) without isolating Compound 21, lactamizing Compound 21 to produce (Compound 18)

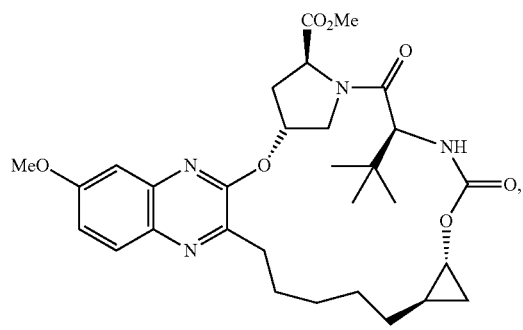

(v) converting Compound 18 to

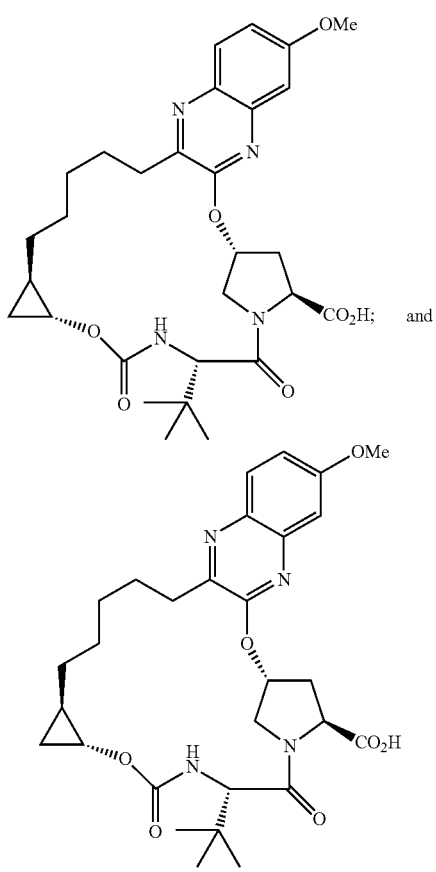 and (vi) coupling

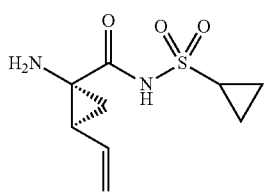

or salt thereof, wherein the coupling of step (vi) comprises the use of a coupling reagent and a compound selected from the group consisting of

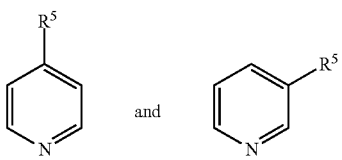

wherein $R^5$ is either hydrogen, aryl, halogen, $C_{1-6}$ alkyl, O—$C_{1-6}$ alkyl or $C_3$-$C_8$ cycloalkyl, and wherein any of Compounds 11, 12, 13, 14, 15, 16, 21, and 18 independently may be provided as salts.

2. The method of claim 1, wherein said coupling reagent is EDC, and the method comprises the use of at least 10 equivalents of pyridine and the use of acetonitrile as solvent.

3. The method of claim 1, wherein said coupling reagent is EDC, and the method comprises the use of THF-DMAc as solvent and a temperature range of −10° C. to 50° C.

4. A compound selected from the group consisting of: a MeCN solvate of a methylsulfonic acid salt of (Compound 14)

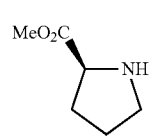

wherein said solvate is characterized by an X-ray powder diffraction pattern obtained using copper Kα radiation which comprises 2Θ values in degrees of about 5.3, 12.0, and 14;

(Compound 16)

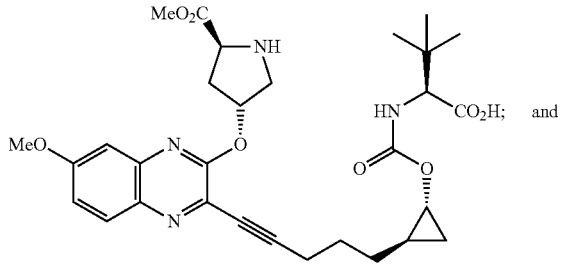

53

-continued (Compound 17)

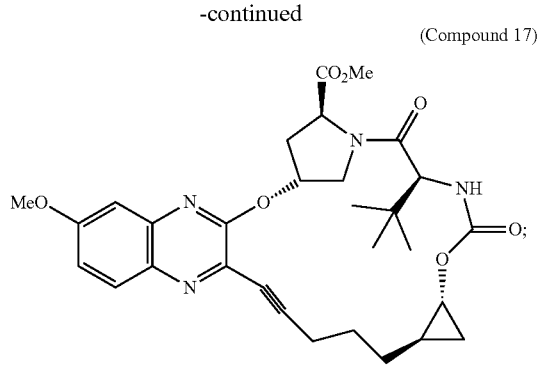

or a salt thereof.

5. The compound of claim 4, wherein said compound is a MeCN solvate of a Compound 14 methylsulfonic acid salt, wherein said solvate is characterized by an X-ray powder diffraction pattern obtained using copper Kα radiation which comprises 2Θ values in degrees of about 5.3, 12.0, and 14.

6. A method of making a compound of claim 4, wherein the compound is Compound 16, said method comprising the step of:

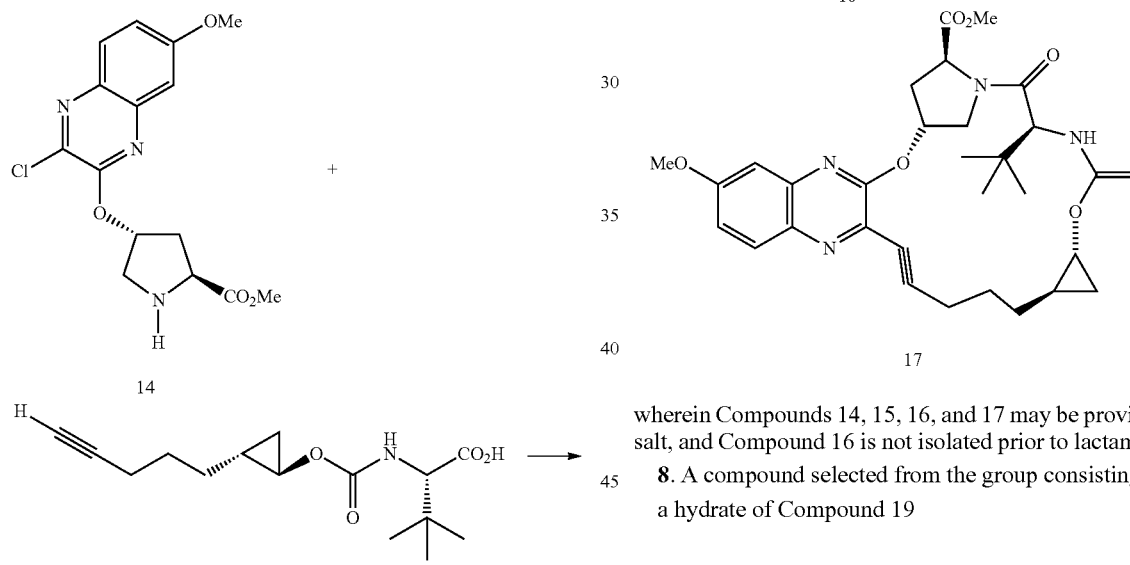

wherein Compounds 14, 15, and 16 may be provided as a salt.

7. A method of making a compound of claim 4, wherein the compound is Compound 17, said method comprising the steps of:

54

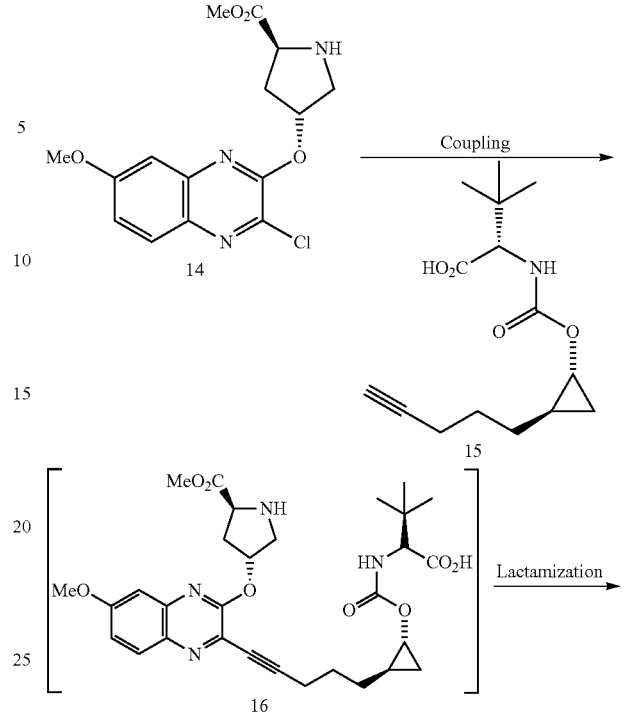

wherein Compounds 14, 15, 16, and 17 may be provided as a salt, and Compound 16 is not isolated prior to lactamization.

8. A compound selected from the group consisting of
a hydrate of Compound 19

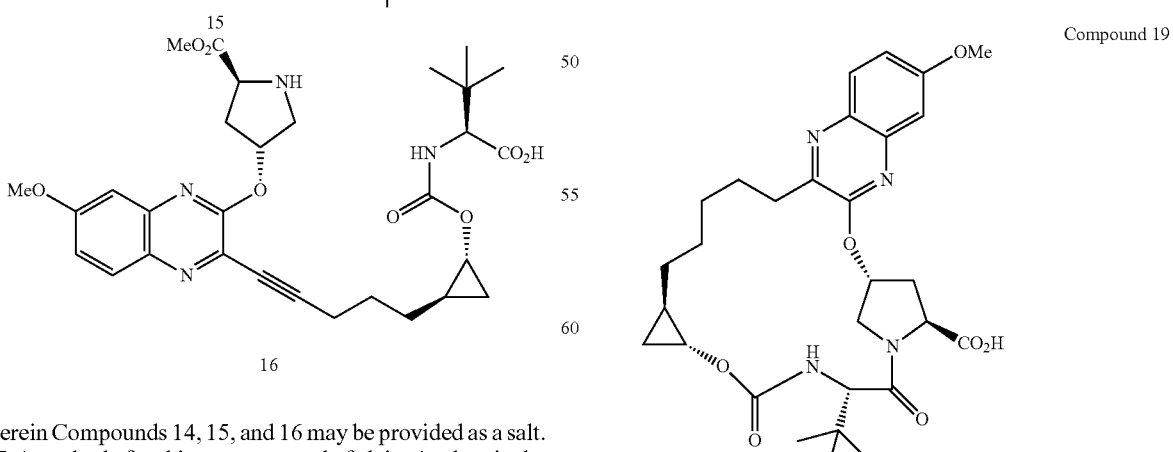

wherein said hydrate of Compound 19 is characterized by either (i) an X-ray powder diffraction pattern obtained using copper Kα radiation which comprises 2Θ values in degrees of about 8.7, 22.2, and 23.5; or (ii) a solid state carbon–13 CPMAS NMR comprising peaks at about 174.7, 172.0, 161.4, 156.8, 156.3, 149.5, 142.1, 133.9, 128.2, 121.3, 105.0, 76.9, 60.7, 57.5, 55.1, 53.5, 35.8, 34.7, 33.4, 32.4, 29.5, 27.8, 24.0, and 20.2 ppm.

* * * * *